(12) United States Patent
Chen et al.

(10) Patent No.: US 7,851,476 B2
(45) Date of Patent: Dec. 14, 2010

(54) CRYSTALLINE FORMS OF 1-BENZOYL-4-[2-[4- METHOXY-7-(3-METHYL-1H-1,2,4-TRIAZOL-1-YL)-1-[(PHOSPHONOOXY)METHYL]-1H-PYRROLO[2,3-C]PYRIDIN-3-YL]-1,2-DIOXOETHYL]-PIPERAZINE

(75) Inventors: Chung-Pin H. Chen, Madison, CT (US); Dawn DiGiugno Parker, Guilford, CT (US); Qi Gao, Wallingford, CT (US); Chong-Hui Gu, Waban, MA (US); Jaquan Kalani Levons, North Brunswick, NJ (US); Bing-Shiou Yang, Dayton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 480 days.

(21) Appl. No.: 11/636,755

(22) Filed: Dec. 11, 2006

(65) Prior Publication Data
US 2007/0155702 A1   Jul. 5, 2007

Related U.S. Application Data

(60) Provisional application No. 60/750,247, filed on Dec. 14, 2005.

(51) Int. Cl.
A61K 31/496   (2006.01)
(52) U.S. Cl. .................. 514/255.06; 544/405; 544/406
(58) Field of Classification Search ................. 544/405, 544/406
See application file for complete search history.

(56) References Cited

U.S. PATENT DOCUMENTS

| | | | |
|---|---|---|---|
| 3,135,794 A | 6/1964 | Archer | |
| 4,791,104 A | 12/1988 | Picciola et al. | |
| 5,023,265 A | 6/1991 | Scherlock et al. | |
| 5,124,327 A | 6/1992 | Greenlee et al. | |
| 5,192,770 A | 3/1993 | Clark et al. | |
| 5,413,999 A | 5/1995 | Vacca et al. | |
| 5,424,329 A | 6/1995 | Boschelli et al. | |
| 5,811,432 A | 9/1998 | Marfat et al. | |
| 6,008,231 A | 12/1999 | Lebaut et al. | |
| 6,172,085 B1 | 1/2001 | Ohkawa et al. | |
| 6,232,327 B1 | 5/2001 | Nickel et al. | |
| 6,469,006 B1 | 10/2002 | Blair et al. | |
| 6,476,034 B2 | 11/2002 | Wang et al. | |
| 6,573,262 B2 | 6/2003 | Wallace et al. | |
| 6,632,819 B1 | 10/2003 | Wang et al. | |
| 6,825,201 B2 | 11/2004 | Wang et al. | |
| 6,900,206 B2 | 5/2005 | Kadow et al. | |
| 7,037,913 B2 | 5/2006 | Wang et al. | |
| 7,087,610 B2 | 8/2006 | Wang et al. | |
| 2002/0061892 A1 | 5/2002 | Wang et al. | |
| 2003/0069266 A1 | 4/2003 | Wang et al. | |
| 2003/0207910 A1 | 11/2003 | Wang et al. | |
| 2003/0236277 A1 | 12/2003 | Kadow et al. | |
| 2004/0063744 A1 | 4/2004 | Wang et al. | |
| 2004/0063746 A1 | 4/2004 | Regueiro-Ren et al. | |
| 2004/0110785 A1 | 6/2004 | Wang et al. | |
| 2004/0186292 A1 | 9/2004 | Wang et al. | |
| 2005/0075364 A1 | 4/2005 | Yeung et al. | |
| 2005/0090522 A1 | 4/2005 | Wang et al. | |
| 2005/0124623 A1 | 6/2005 | Bender et al. | |
| 2005/0209246 A1 | 9/2005 | Ueda et al. | |
| 2005/0215543 A1 | 9/2005 | Lin et al. | |
| 2005/0215544 A1 | 9/2005 | Lin et al. | |
| 2005/0215545 A1 | 9/2005 | Lin et al. | |
| 2005/0267130 A1 | 12/2005 | Ruediger et al. | |
| 2006/0100209 A1 | 5/2006 | Gu et al. | |
| 2006/0100432 A1 | 5/2006 | Matiskella et al. | |
| 2006/0142298 A1 | 6/2006 | Kadow et al. | |
| 2007/0078141 A1 | 4/2007 | Wang et al. | |
| 2007/0249579 A1 | 10/2007 | Wang et al. | |
| 2007/0249624 A1 | 10/2007 | Bachand et al. | |

FOREIGN PATENT DOCUMENTS

| | | |
|---|---|---|
| EP | 0379314 A1 | 7/1990 |
| EP | 0484071 A2 | 5/1992 |
| EP | 0530907 A1 | 3/1993 |
| EP | 1069111 A1 | 1/2001 |
| WO | WO 93/01181 | 1/1993 |
| WO | WO 95/04742 | 2/1995 |

(Continued)

OTHER PUBLICATIONS

U.S. Appl. No. 11/748,699.

(Continued)

*Primary Examiner*—James O Wilson
*Assistant Examiner*—Brian McDowell
(74) *Attorney, Agent, or Firm*—John F. Levis

(57) ABSTRACT

Crystalline forms of 1-benzoyl-4-[2-[4-methoxy-7-(3-methyl-1H-1,2,4-triazol-1-yl)-1-[(phosphonooxy)methyl]-1H-pyrrolo[2,3-c]pyridin-3-yl]-1,2-dioxoethyl]-piperazine

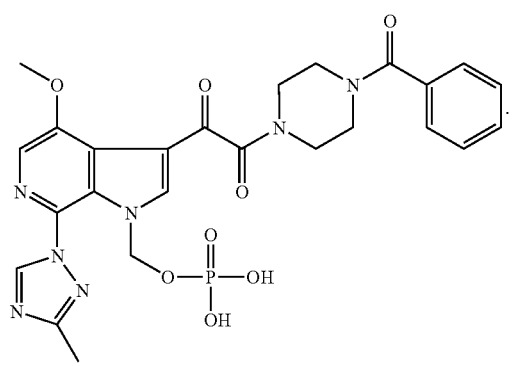

its salts and solvates thereof are herein set forth, as are pharmaceutical compositions comprising the crystalline form(s), as well of methods of using the crystalline form(s) in the treatment of HIV and/or AIDS, and methods for obtaining such crystalline form(s).

14 Claims, 13 Drawing Sheets

FOREIGN PATENT DOCUMENTS

| WO | WO 96/11929 | 4/1996 |
|---|---|---|
| WO | WO 97/25350 | 7/1997 |
| WO | WO 98/28292 | 7/1998 |
| WO | WO 99/24065 | 5/1999 |
| WO | WO 00/00201 | 1/2000 |
| WO | WO 00/12074 | 3/2000 |
| WO | WO 00/51984 | 9/2000 |
| WO | WO 00/71535 | 11/2000 |
| WO | WO 00/76521 A1 | 12/2000 |
| WO | WO 01/22954 A2 | 4/2001 |
| WO | WO 01/62255 | 8/2001 |
| WO | WO 02/04440 | 1/2002 |
| WO | WO 02/10152 A2 | 2/2002 |
| WO | WO 02/62423 | 8/2002 |
| WO | WO 02/085301 A2 | 10/2002 |
| WO | WO 03/041644 | 5/2003 |
| WO | WO 03/068221 A1 | 8/2003 |
| WO | WO 03/082881 A | 10/2003 |
| WO | WO 03/092695 | 11/2003 |
| WO | WO 03/103607 | 12/2003 |
| WO | WO 2004/000210 A2 | 12/2003 |
| WO | WO 2004/011425 A2 | 2/2004 |
| WO | WO 2004/043337 A2 | 5/2004 |
| WO | WO 2005/016344 | 2/2005 |
| WO | WO 2005/121094 | 12/2005 |

OTHER PUBLICATIONS

U.S. Appl. No. 11/749,445.
Heimbach, et al, "Absorption Rate Limit Considerations for Oral Phosphate Prodrugs," Pharmaceutical Research, 20(6), pp. 848-856, 2003.
Stella, et al, Pharmacokinetics of Drug Targeting: Specific Implications for Targeting Via Prodrugs, Handbook of Experimental Pharmacology, Chapter 4, pp. 71-103, 1991.
Zhu, et al, "A One-Pot Synthesis of Nitrogen-Containing Heteroaryl α-Keto Amides from Heteroaryl Halides," Tetrahedron Letters, 46(20), pp. 3587-3589, 2005.
Yin, et al., "Simulated PXRD Patterns in Studies of the Phase Composition and Thermal Behavior of Bulk Crystalline Solids," American Pharmaceutical Review, 2003, 6, 2, pp. 80-85.
Hotoda, "Small-Molecule Inhibitors of HIV-1 Entry Via Chemokine Receptors," Drugs of the Fututre, 24(12), pp. 1355-1362, 1999.
Sodroski, "HIV-1 Entry Inhibitors in the Side Pocket," Cell, 9, pp. 243-246, 1999.
Blair, et al, "HIV-1 Entry-An Expanding Portal for Drug Discovery," Drug Discovery Today, 5(5), pp. 183-194, 2000.
Font, et al, "Indoles and Pyridazinol[4,5-b]Indoles as Nonnucleoside Analog Inhibitors of HIV-1 Reverse Transcriptase," Eur. J. Med. Chem., 30, pp. 963-971, 1995.
Romero, et al, J. Med. Chem., 36, pp. 1505-1508, 1993.
Young, et al, "2-Heterocyclic Indole-3-Sulfones as Inhibitors of HIV-1 Reverse Transcriptase," Bioorg. Med. Chem. Lett., 5(5), pp. 491-496, 1995.
Genin, et al, "Synthesis and Bioactivity of Novel Bis(Heteroaryl)Piperazine (BHAP) Reverse Transcriptase Inhibitors: Structure-Activity Relationships and Increased Metabolic Stability of Novel Substituted Pyridine Analogs," J. Med. Chem., 39, pp. 5267-5275, 1996.
Silvestri, et al, Antiviral Chem. Chemother., 9, pp. 139-148, 1998.
Fredenhagen, et al, "Semicochllodinol A and B: Inhibitors of HIV-1 Protease and EGF-R Protein Tyrosine Kinase Related to Asterriquinones Produced by the Fungus Chrysosporium Merdarium," J. of Antibiotics, 50, pp. 395-401, 1997.
Wang, et al., Org. Biol. Chem., 2005, 3, pp. 1781-1786.
Meanwell et al., Current Opinion in Drug Discovery and Development, 2003, 6, 4, pp. 451-461.
Dueweke, et al, "The Binding of a Novel Bisheteroarylpiperazine Mediates Inhibition of Human Immunodeficiency Virus Type 1 Reverse Transcriptase," J. Biol. Chem., 267(1), pp. 27-30, 1992.
Dueweke, et al, "U-90152, a Potent Inhibitor of Human Immunodeficiency Virus type 1 Replication," Antimicrob. Agent, Chemother., 37(5), pp. 1127-1131, 1993.
Kato, et al, "New 5-$HT_3$ (Serotonin-3) Receptor Antagonists. IV. Synthesis and Structure-Activity Relationships of Azabicycloalkaneacetamide Derivatives," Chem. Pharm. Bull., 43(8), pp. 1351-1357, 1995.
Levacher, et al, "Broadening in the Scope of NADH Models by Using Chiral and Non Chiral Pyrrolo [2,3-b]Pyridine Derivatives," Tetrahedron, 47(3), pp. 429-440, 1991.
Resnyanskaya, et al, "A Simple Synthesis of 1-Acyl-3-Aryl-3H-Pyrrolo[2',3':4,5]Pyrimido[6,1-b]Benzothiazol-6-ium-2-olates: Betainic Derivatives of a Novel Heterocyclic System," Synthesis, 18, pp. 2717-2724, 2002.

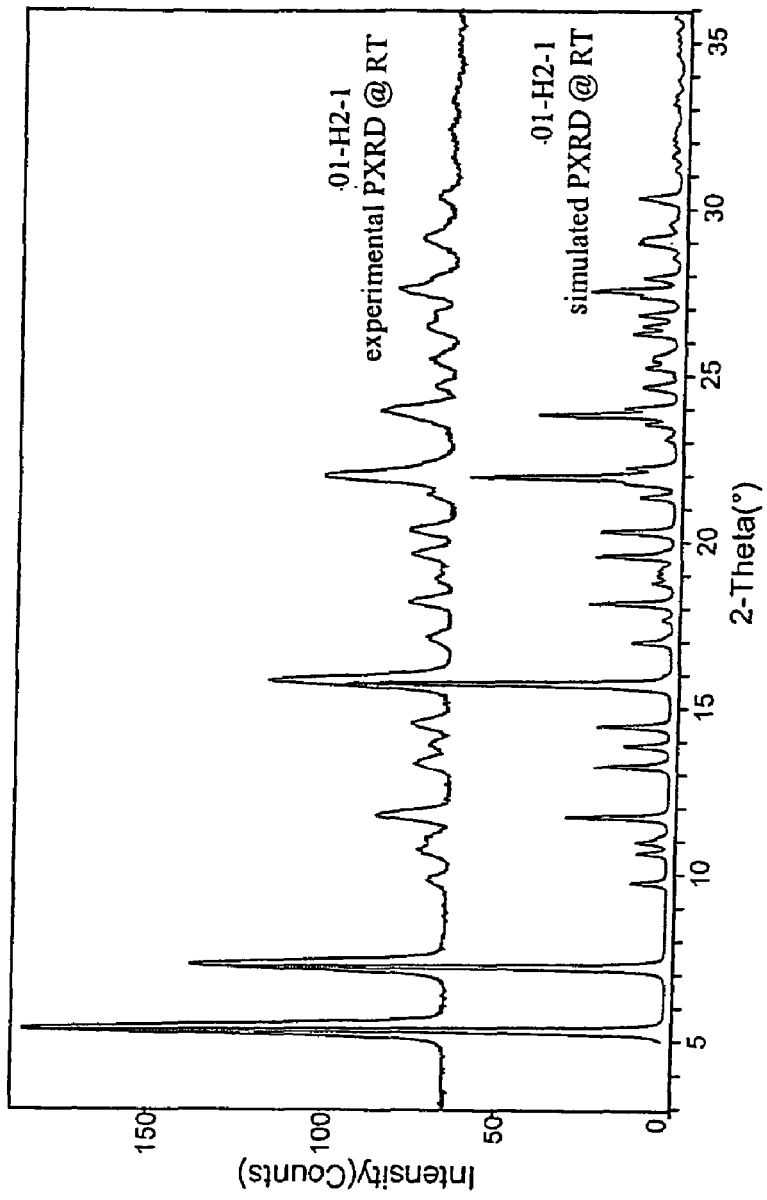
FIG 1. PXRD of Form 01-H2-1 (a dihydrate form of free acid)

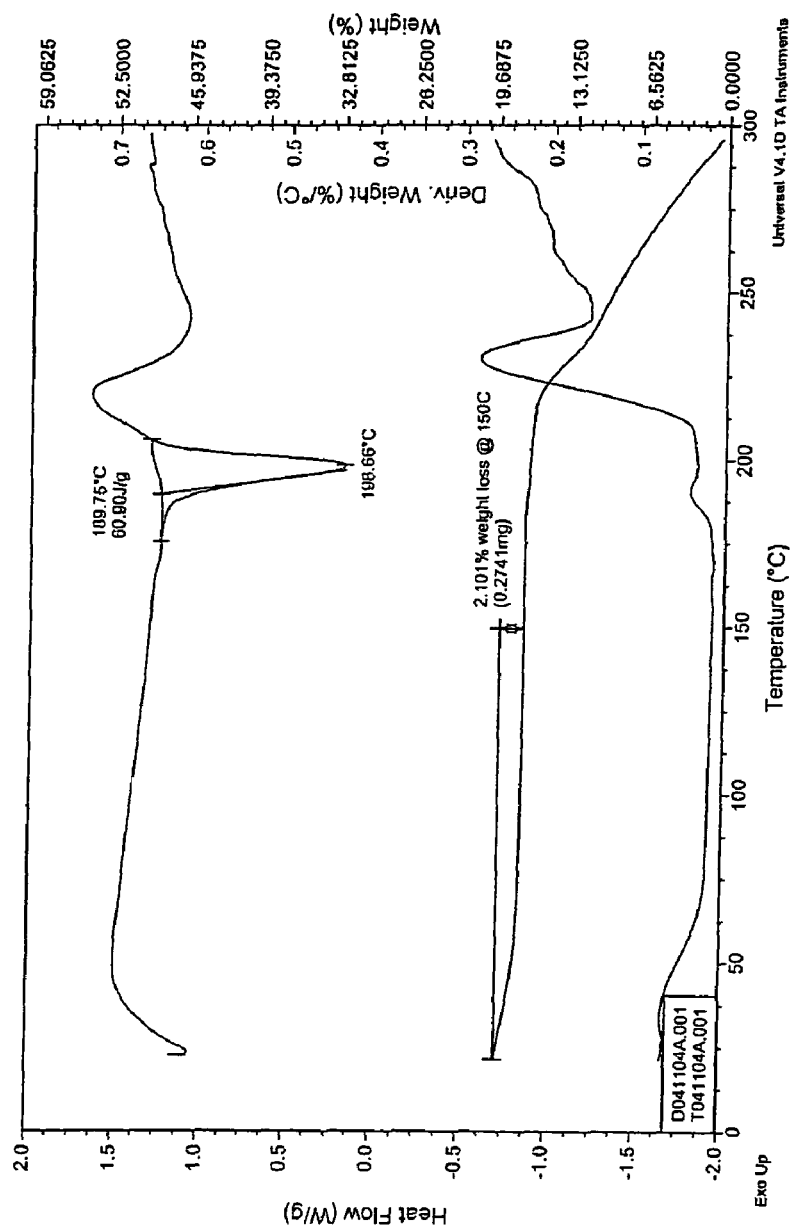
FIG 2. DSC/TGA of Form 01-H2-1 (a dihydrate form of free acid)

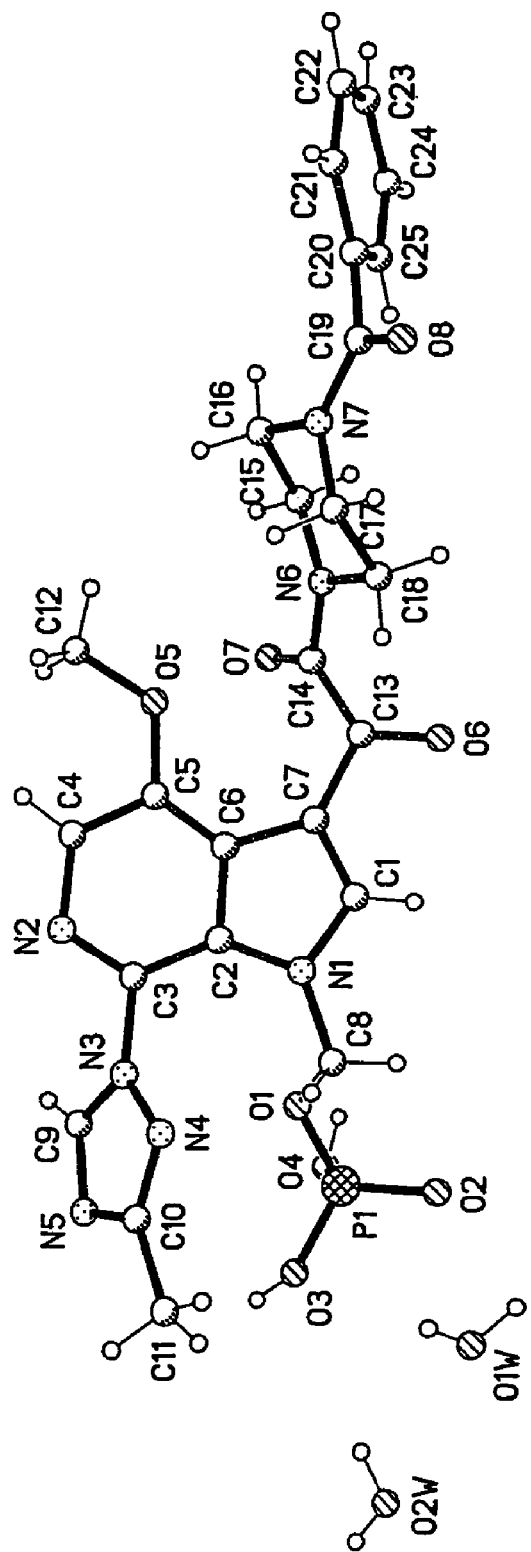
FIG. 3. Atom Labels, Form 01-H2-1

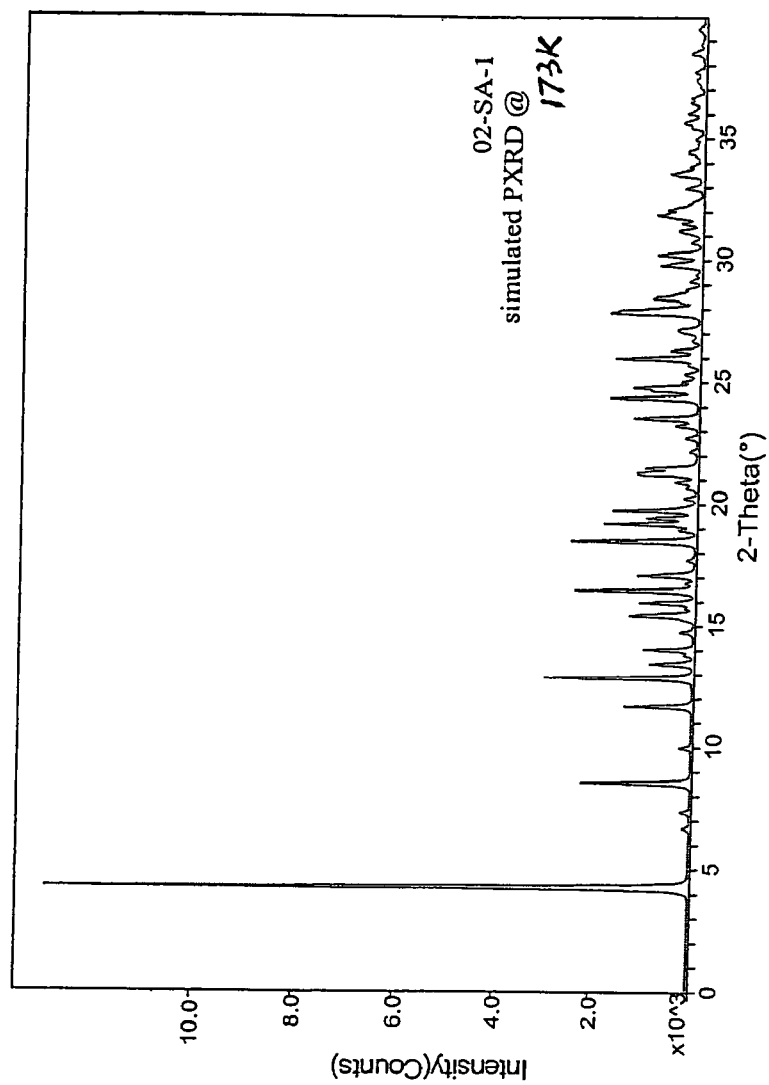
FIG 4. PXRD of Form 02-SA-1 (a hemiethanolate octahydrate of di-sodium salt)

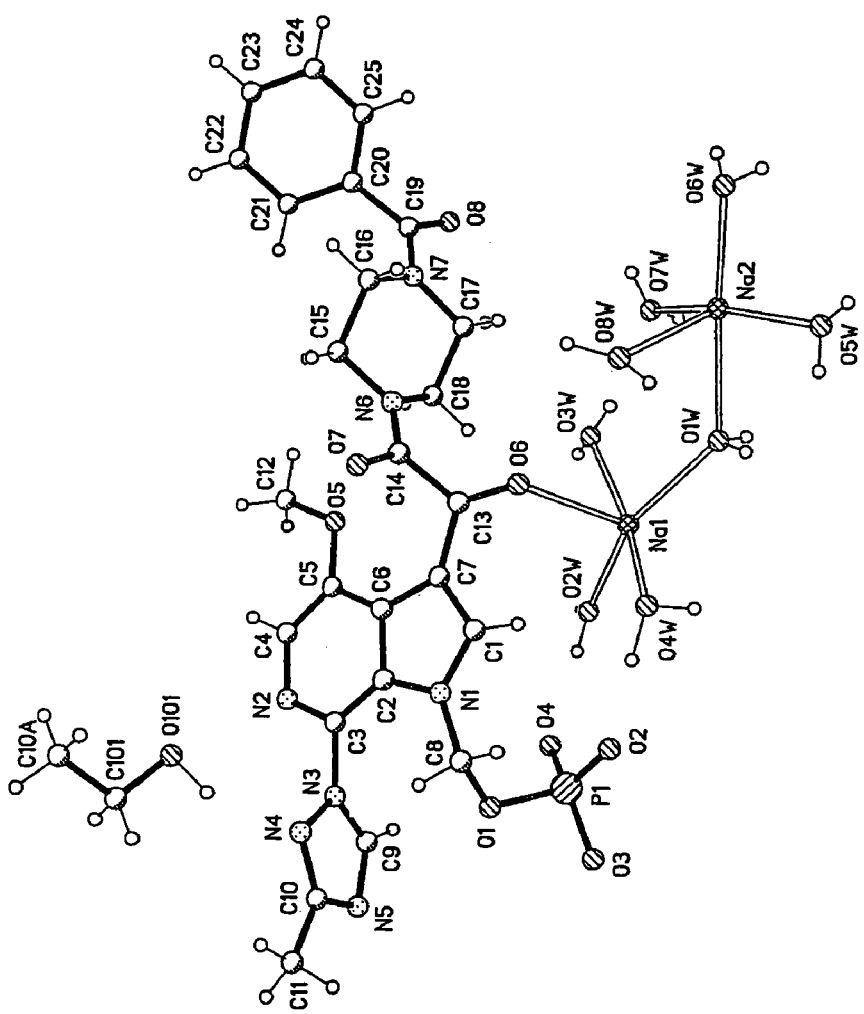
FIG 5. Atom Labels, Form 02-SA-1

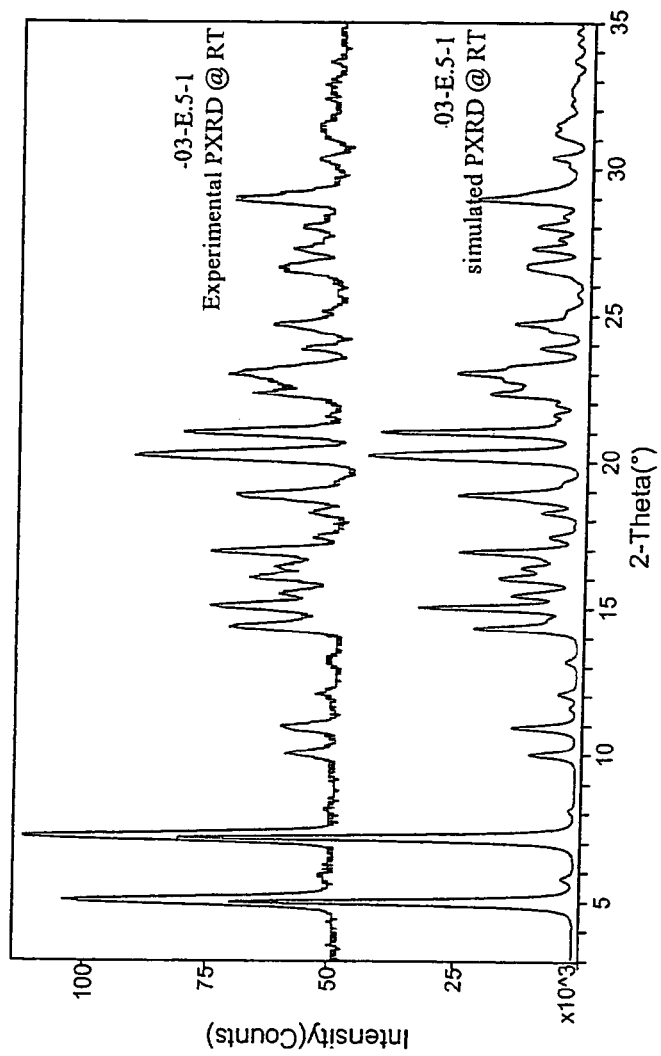
FIG 6. PXRD of Form 03-E.5-1 (a hemiethanolate of mono-TRIS salt)

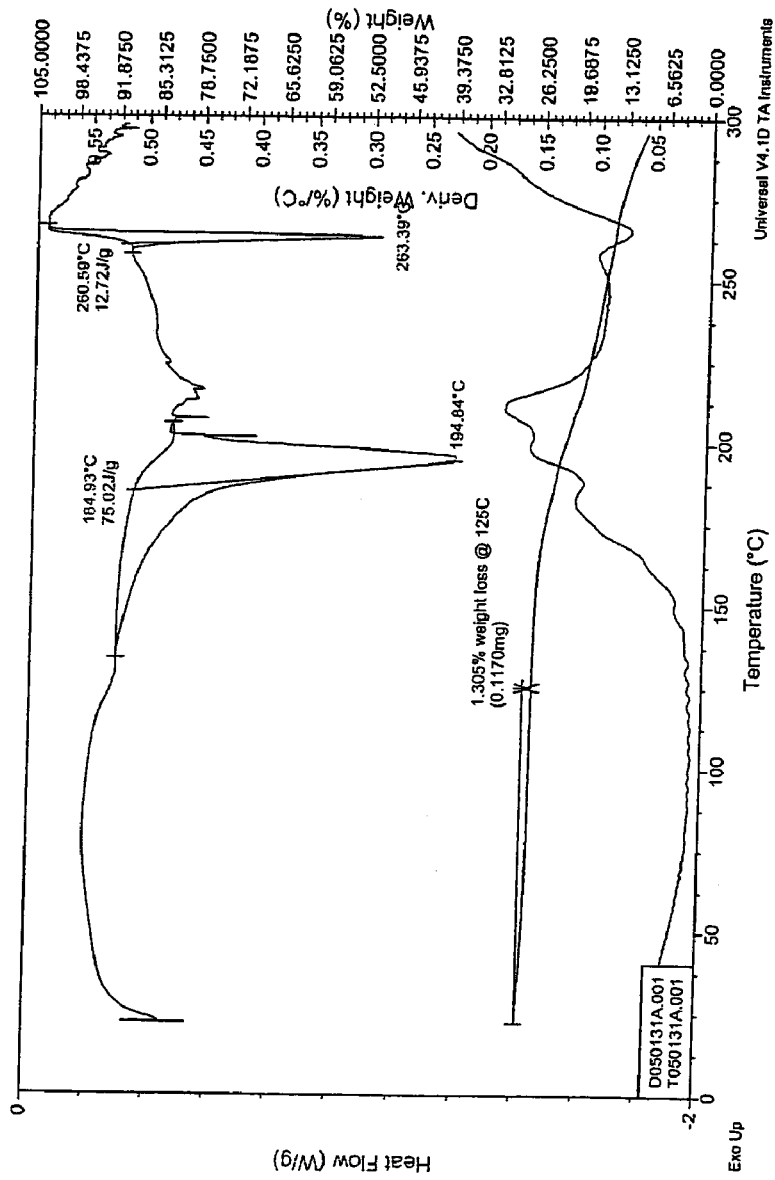
FIG 7. DSC/TGA of Form 03-E.5-1 (a hemiethanolate of mono-TRIS salt)

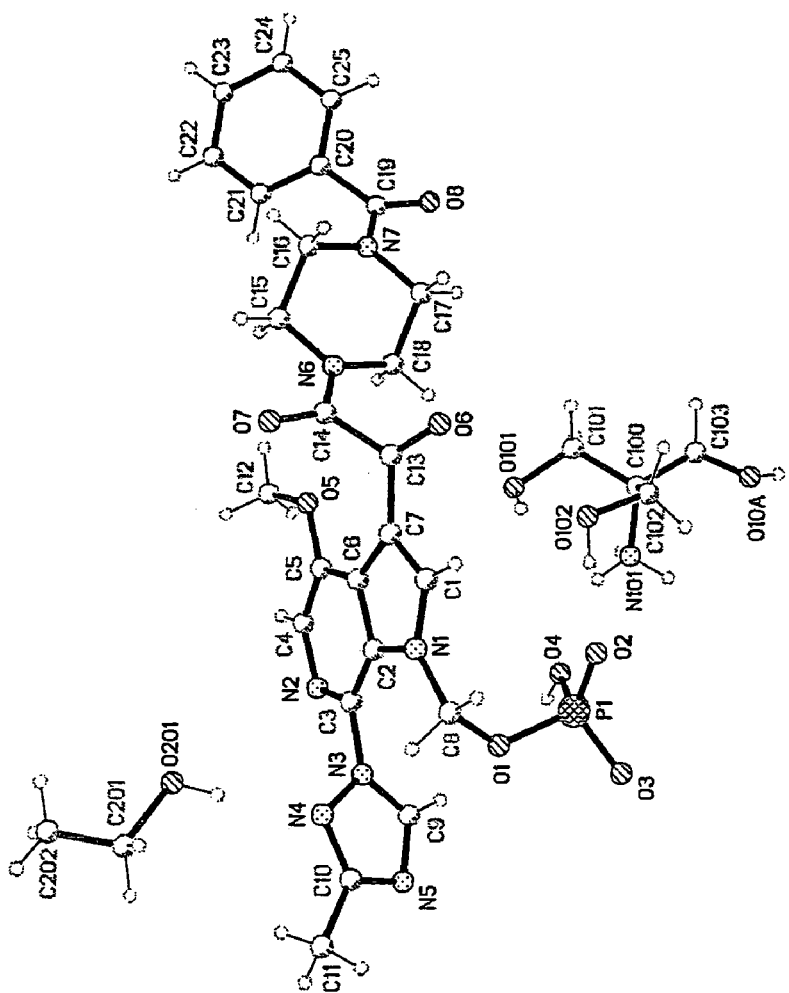
FIG. 8. Atom Labels, Form 03-E.5-1

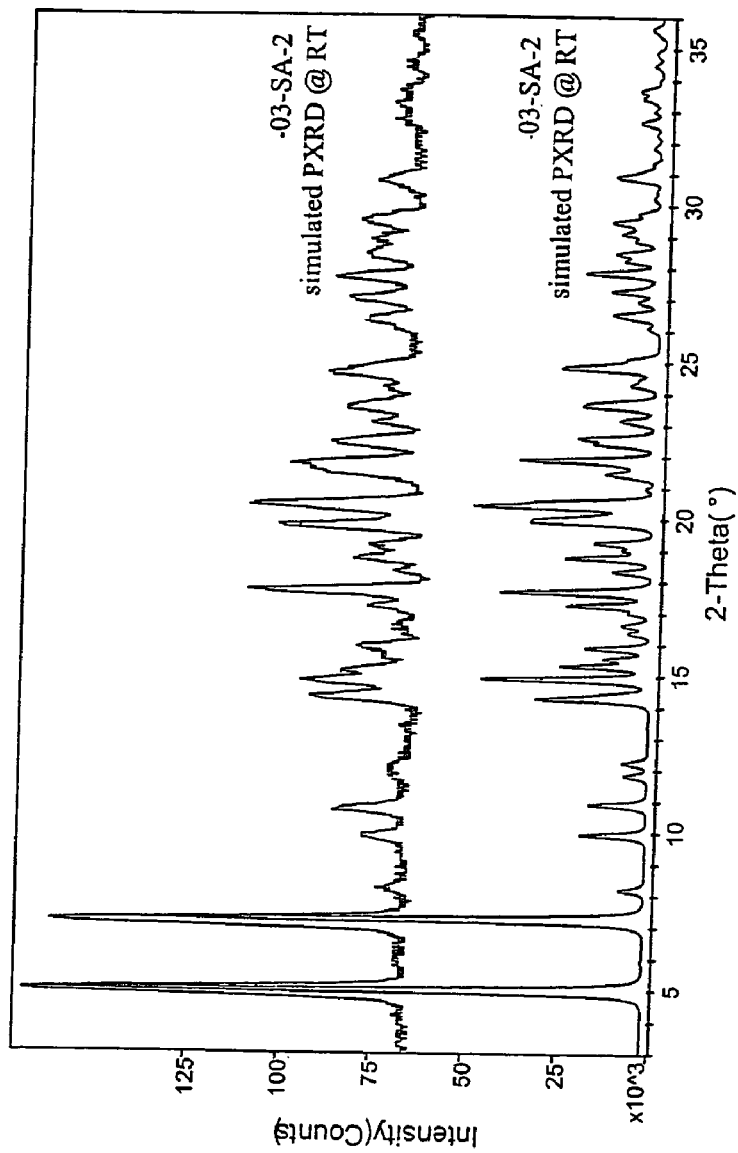
FIG 9. PXRD of Form 03-SA-2 (a hemiacetonate hemihydrate of mono-TRIS salt)

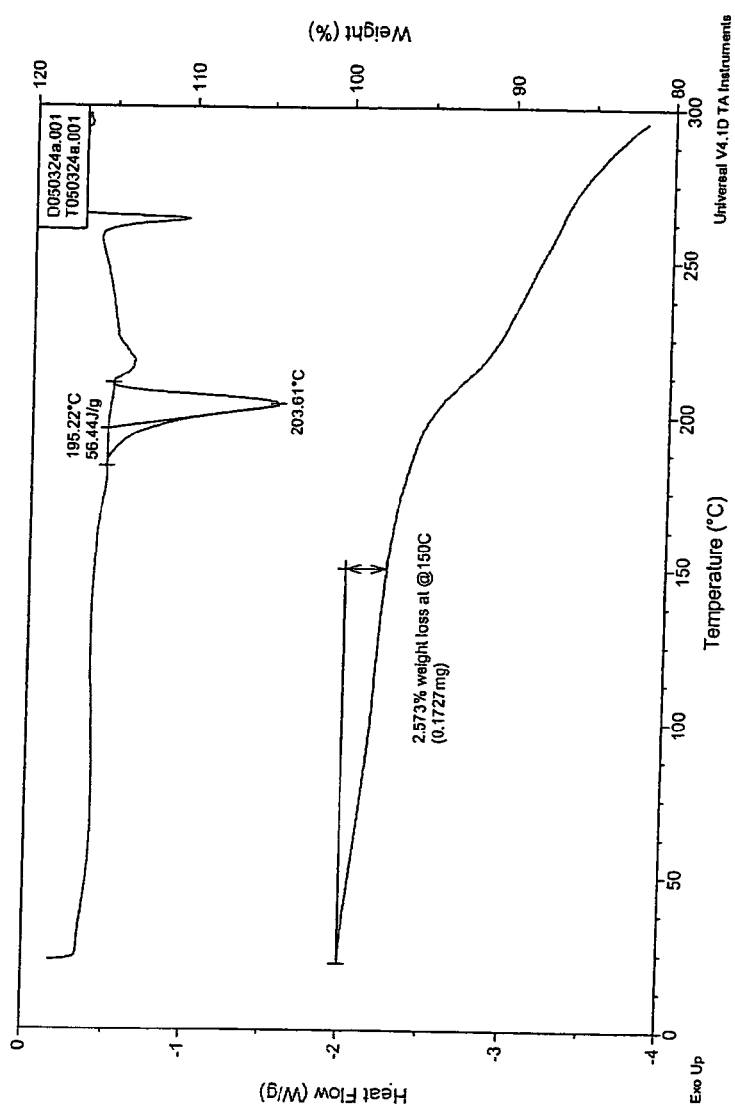
FIG 10. DSC/TGA of BMS-663068-03-SA-2 (a hemiacetonate hemihydrate of mono-TRIS salt)

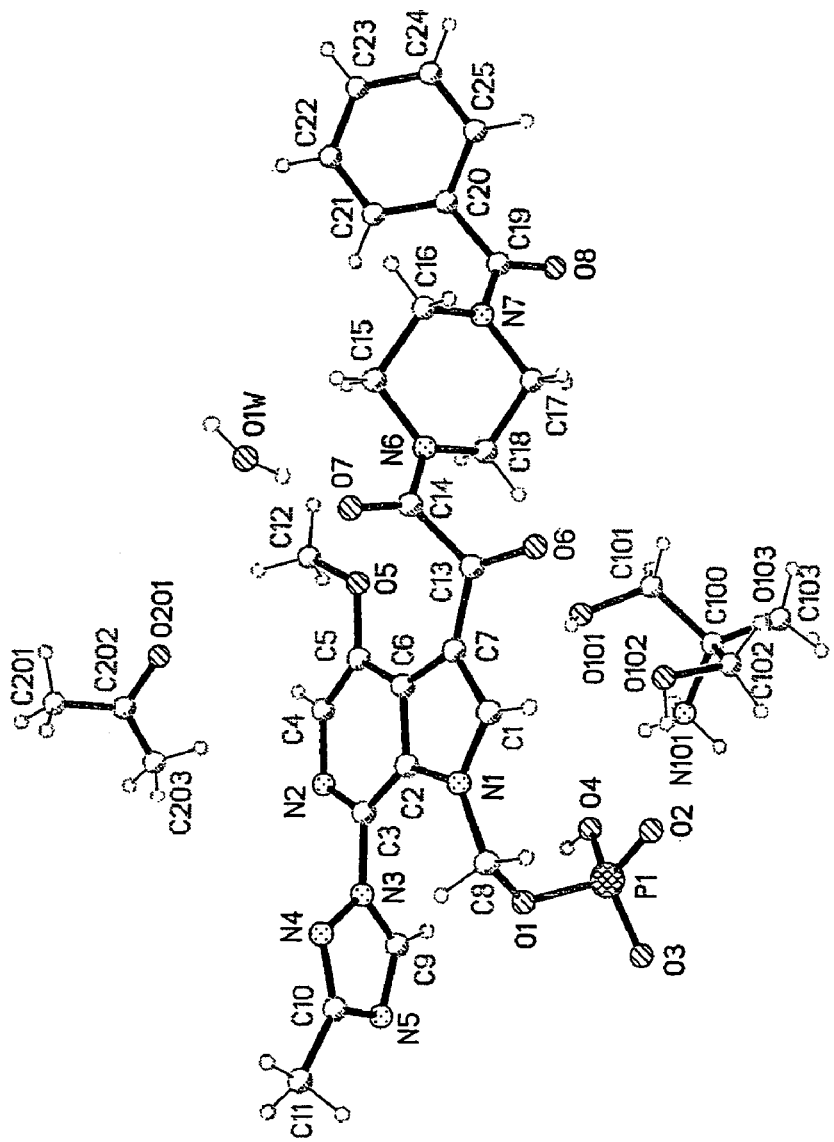
FIG. 11. Atom Labels, Form 03-SA-2

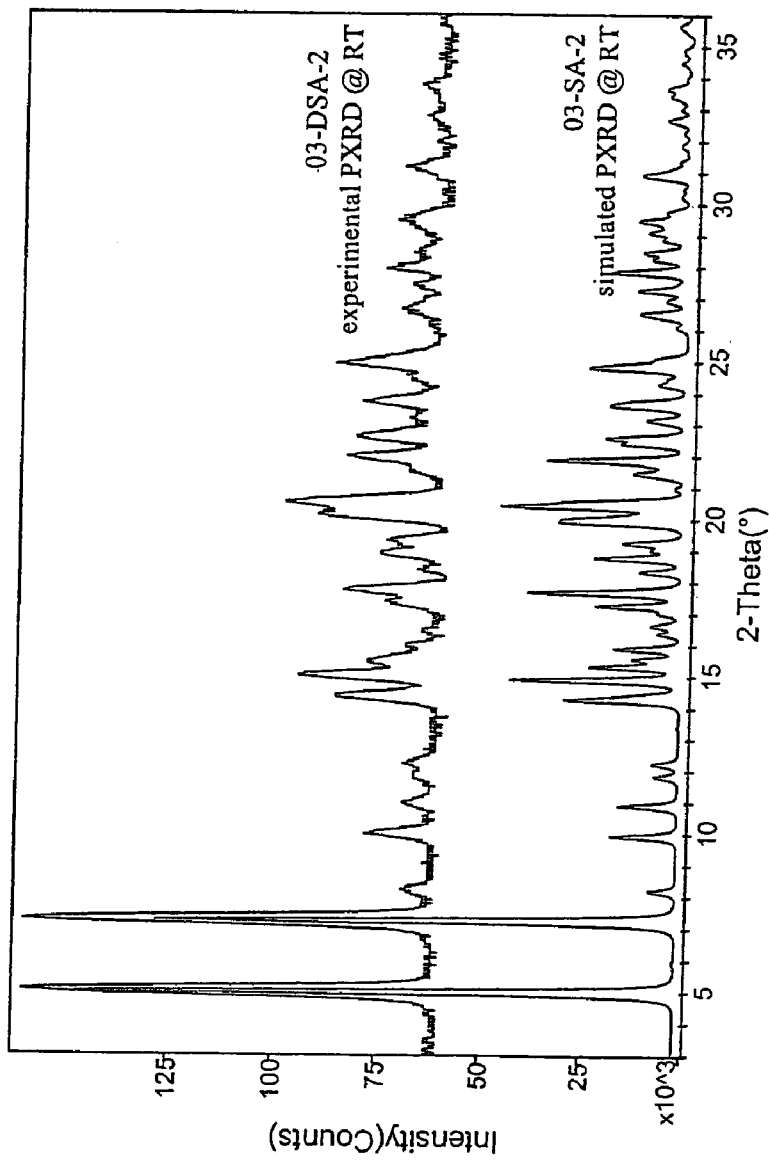
FIG 12. PXRD of Form 03-DSA-2
(a dehydrated and desolvated form of Form 03-SA-2)

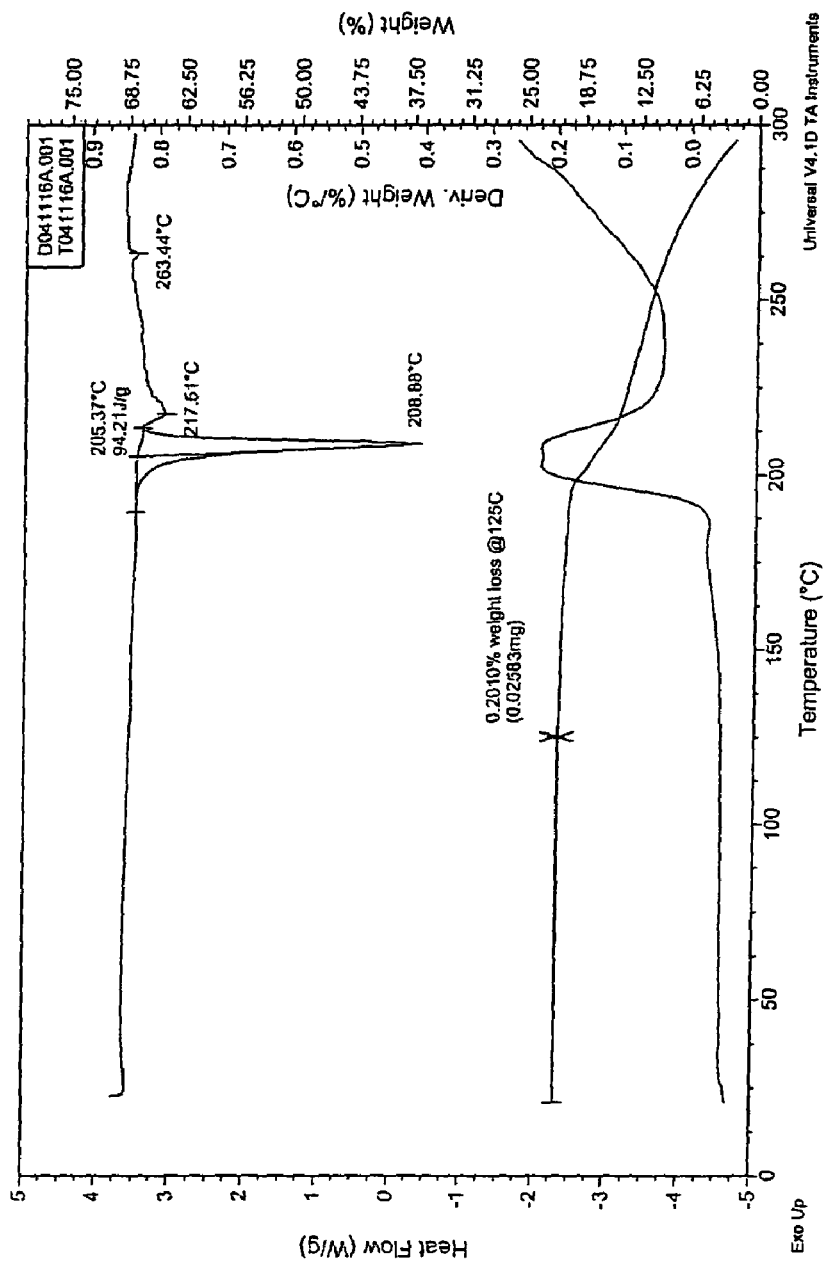
FIG 13. DSC/TGA of Form 03-DSA-2 (a dehydrated and desolvated form of Form 03-SA-2)

CRYSTALLINE FORMS OF 1-BENZOYL-4-[2-[4-METHOXY-7-(3-METHYL-1H-1,2,4-TRIAZOL-1-YL)-1-[(PHOSPHONOOXY)METHYL]-1H-PYRROLO[2,3-C]PYRIDIN-3-YL]-1,2-DIOXOETHYL]-PIPERAZINE

CROSS-REFERENCE TO RELATED APPLICATIONS

This application claims the benefit of U.S. Provisional Application Ser. No. 60/750,247 filed Dec. 14, 2005.

FIELD OF INDUSTRIAL APPLICABILITY

The present invention generally relates to crystalline forms of 1-benzoyl-4-[2-[4-methoxy-7-(3-methyl-1H-1,2,4-triazol-1-yl)-1-[(phosphonooxy)methyl]-1H-pyrrolo[2,3-c]pyridin-3-yl]-1,2-dioxoethyl]-piperazine. The present invention also generally relates to a pharmaceutical composition comprising the crystalline forms, as well of methods of using the crystalline forms in the treatment of HIV and/or AIDS, and methods for obtaining such crystalline forms.

BACKGROUND OF THE INVENTION

HIV-1 (human immunodeficiency virus-1) infection remains a major medical problem, with an estimated 42 million people infected worldwide at the end of 2002. The number of cases of HIV and AIDS (acquired immunodeficiency syndrome) has risen rapidly. In 2002, ~5.0 million new infections were reported, and 3.1 million people died from AIDS. Currently available drugs for the treatment of HIV include nine nucleoside reverse transcriptase (RT) inhibitors or approved single pill combinations (zidovudine or AZT (or Retrovir®), didanosine (or Videx®), stavudine (or Zerit®), lamivudine (or 3TC or Epivir®), zalcitabine (or DDC or Hivid®), abacavir succinate (or Ziagen®), Tenofovir disoproxil fumarate salt (or Viread®), Combivir® (contains -3TC plus AZT), Trizivir® (contains abacavir, lamivudine, and zidovudine); three non-nucleoside reverse transcriptase inhibitors: nevirapine (or Viramune®), delavirdine (or Rescriptor®) and efavirenz (or Sustiva®), and eight peptidomimetic protease inhibitors or approved formulations: saquinavir, indinavir, ritonavir, nelfinavir, ainprenavir, lopinavir, Kaletra® (lopinavir and Ritonavir), and Atazanavir (Reyataz®). Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present (Larder and Kemp; Gulick; Kuritzkes; Morris-Jones et al. Schinazi et al; Vacca and Condra; Flexner; Berkhout and Ren et al. (Ref. 6-14)). Therefore, novel anti-HIV agents exhibiting distinct resistance patterns, and favorable pharmacokinetic as well as safety profiles are needed to provide more treatment options.

U.S. application Ser. No. 11/066,745, filed Feb. 25, 2005 (claiming the benefit of U.S. Provisional Application Ser. Nos. 60/635,231 filed Dec. 10, 2004 and 60/553,320 filed Mar. 15, 2004, and incorporated herein by reference in its entirety) discloses a class of compounds (or pharmaceutically acceptable salts thereof) of the formula:

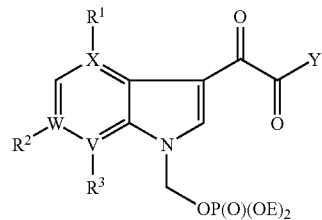

wherein:

X is C or N with the proviso that when X is N, $R^1$ does not exist;

W is C or N with the proviso that when W is N, $R^2$ does not exist;

V is C;

$R^1$ is hydrogen, methoxy or halogen;

$R^2$ is hydrogen;

$R^3$ is methoxy or heteroaryl, each of which may be independently optionally substituted with one substituent selected from G; wherein heteroaryl is triazolyl, pyrazolyl or oxadiazolyl;

E is hydrogen or a pharmaceutically acceptable mono or bis salt thereof;

Y is selected from the group consisting of

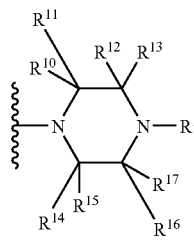 and 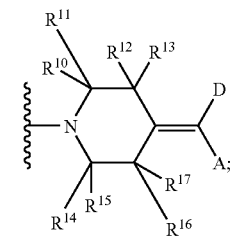

$R^{10}$, $R^{11}$, $R^{12}$, $R^{13}$, $R^{14}$, $R^{15}$, $R^{16}$, $R^{17}$ are each independently H or methyl, with the proviso that not more than two of $R^{10}$-$R^{17}$ are methyl;

$R^{18}$ is selected from the group consisting of C(O)-phenyl, C(O)-pyridinyl, pyridinyl, pyrimidinyl, quinolinyl, isoquinolinyl, quinazolinyl, quinoxalinyl, napthyridinyl, pthalazinyl, azabenzofuryl and azaindolyl, each of which may be independently optionally substituted with from one to two members selected from the group consisting of methyl, -amino, —NHMe, —NMe$_2$, methoxy, hydroxymethyl and halogen;

D is selected from the group consisting of cyano, $S(O)_2R^{24}$, halogen, $C(O)NR^{21}R^{22}$, phenyl and heteroaryl; wherein said phenyl or heteroaryl is independently optionally substituted with one to three same or different halogens or from one to three same or different substituents selected from G; wherein heteroaryl is selected from the group consisting of pyridinyl and oxadiazolyl;

A is selected from the group consisting of phenyl, pyridinyl, furyl, thienyl, isoxazolyl and oxazolyl wherein said phenyl, pyridinyl, furyl, thienyl, isoxazolyl and oxazolyl are independently optionally substituted with one to three same or different halogens or from one to three same or different substituents selected from G;

G is selected from the group consisting of $(C_{1-6})$alkyl, $(C_{1-6})$alkenyl, phenyl, hydroxy, methoxy, halogen, —$NR^{23}C(O)$—$(C_{1-6})$alkyl, —$NR^{24}R^{25}$, —$S(O)_2NR^{24}R^{25}$, $COOR^{26}$ and —$CONR^{24}R^{25}$; wherein said $(C_{1-6})$alkyl is optionally substituted with hydroxy, dimethylamino or one to three same or different halogen;

$R^{26}$ is selected from the group consisting of hydrogen and $(C_{1-6})$alkyl;

$R^{20}$, $R^{21}$, $R^{22}$, $R^{23}$, $R^{24}$, $R^{25}$ are independently selected from the group consisting of hydrogen, $(C_{1-6})$alkyl and —$(CH_2)_nNR^{27}R^{28}$;

n is 0-6; and $R^{27}$ and $R^{28}$ are each independently H or methyl.

U.S. application Ser. No. 11/066,745 also specifically discloses the compound

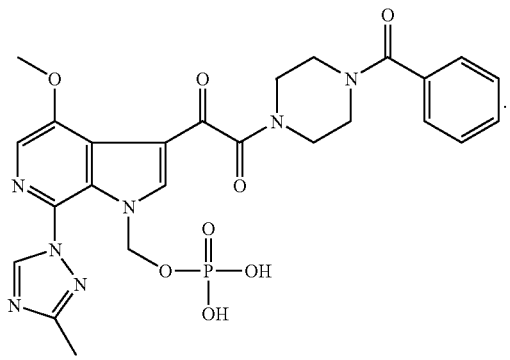

There exists a need for different forms of the compound 1-benzoyl-4-[2-[4-methoxy-7-(3-methyl-1H-1,2,4-triazol-1-yl)-1-[(phosphonooxy)methyl]-1H-pyrrolo[2,3-c]pyridin-3-yl]-1,2-dioxoethyl]-piperazine (IUPAC name: (3-((4-benzoylpiperazin-1-yl)(oxo)acetyl)-4-methoxy-7-(3-methyl-1H-1,2,4-triazol-1-yl)-1H-pyrrolo[2,3-c]pyridin-1-yl) methyl dihydrogen phosphate), salts and solvates thereof, since the different forms may have different physical and/or chemical properties. There is also a need to produce a stable form of 1-benzoyl-4-[2-[4-methoxy-7-(3-methyl-1H-1,2,4-triazol-1-yl)-1-[(phosphonooxy)methyl]-1H-pyrrolo[2,3-c]pyridin-3-yl]-1,2-dioxoethyl]-piperazine, salts and solvates thereof for long term storage etc. There is also a need for reliable and reproducible methods for the manufacture, purification, and formulation to permit its feasible commercialization.

SUMMARY OF THE INVENTION

The present invention provides crystalline forms of 1-benzoyl-4-[2-[4-methoxy-7-(3-methyl-1H-1,2,4-triazol-1-yl)-1-[(phosphonooxy)methyl]-1H-pyrrolo[2,3-c]pyridin-3-yl]-1,2-dioxoethyl]-piperazine, salts and solvates thereof. Embodiments of these crystalline forms include those characterized herein as Forms-01-H2-1, -02-SA-1, -03-E.5-1, -03-SA-2, and -03-DSA-2 etc. The names used herein to characterize a specific form, e.g. "-01-H2-1" etc., should not be considered limiting with respect to any other substance possessing similar or identical physical and chemical characteristics, but rather it should be understood that these designations are mere identifiers that should be interpreted according to the characterization information also presented herein.

1-benzoyl-4-[2-[4-methoxy-7-(3-methyl-1H-1,2,4-triazol-1-yl)-1-[(phosphonooxy)methyl]-1H-pyrrolo[2,3-c]pyridin-3-yl]-1,2-dioxoethyl]-piperazine is identified as Compound (I) herein and is described by Formula (I):

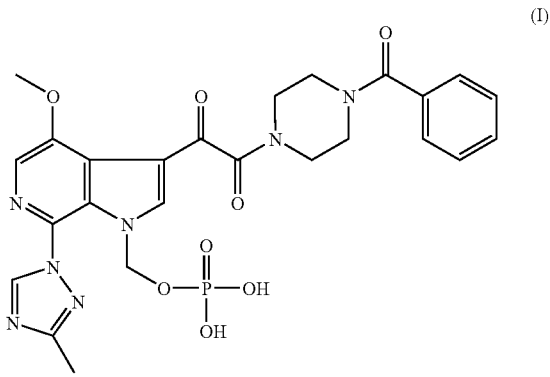

In a first embodiment, the present disclosure relates to a crystalline form of Compound (I) comprising Form 01-H2-1 of Compound (I).

In a second embodiment, the present disclosure relates to a crystalline form of Compound (I) comprising Form 02-SA-1 of Compound (I).

In a third embodiment, the present disclosure relates to a crystalline form of Compound (I) comprising Form 03-E.5-1 of Compound (I).

In a fourth embodiment, the present disclosure relates to a crystalline form of Compound (I) comprising Form 03-SA-2 of Compound (I).

In a fifth embodiment, the present disclosure relates to a crystalline form of Compound (I) comprising Form 03-DSA-2 of Compound (I).

These and other aspects of the disclosure will become more apparent from the following detailed description.

BRIEF DESCRIPTION OF THE DRAWINGS

The invention is illustrated by reference to the accompanying drawings described below.

FIG. 1. illustrates experimental and simulated powdered X-ray diffraction patterns (CuKα λ=1.5418 Å at T=293 K) of Form 01-H2-1 of Compound (I).

FIG. 2. illustrates differential scanning calorimetry pattern and thermogravimetric analysis pattern of Form 01-H2-1 of Compound (I).

FIG. 3. illustrates the labeling of atoms (except H atoms) in Form 01-H2-1 of Compound (I).

FIG. 4. illustrates simulated powdered X-ray diffraction patterns (CuKα λ=1.5418 Å at T=173 K) of Form 02-SA-1 of Compound (I).

FIG. 5. illustrates the labeling of atoms (except H atoms) in Form 02-SA-1 of Compound (I).

FIG. 6. illustrates experimental and simulated powdered X-ray diffraction patterns (CuKα λ=1.5418 Å at T=293 K) of Form 03-E.5-1 of Compound (I).

FIG. 7. illustrates differential scanning calorimetry pattern and thermogravimetric analysis pattern of Form 03-E.5-1 of Compound (I).

FIG. 8. illustrates the labeling of atoms (except H atoms) in Form 03-E.5-1 of Compound (I).

FIG. 9. illustrates experimental and simulated powdered X-ray diffraction patterns (CuKα λ=5418 Å at T=293 K) of Form 03-SA-2 of Compound (I).

FIG. 10. illustrates differential scanning calorimetry pattern and thermogravimetric analysis pattern of Form 03-SA-2 of Compound (I).

FIG. 11. illustrates the labeling of atoms (except H atoms) in Form 03-SA-2 of Compound (I).

FIG. 12. illustrates experimental and simulated powdered X-ray diffraction patterns (CuKα λ=1.5418 Å at T=293 K) of Form 03-DSA-2 of Compound (I).

FIG. 13. illustrates differential scanning calorimetry pattern and thermogravimetric analysis pattern of Form 03-DSA-2 of Compound (I).

DETAILED DESCRIPTION OF THE INVENTION

The present disclosure provides, at least in part, crystalline forms of Compound (I), salts and solvates thereof. The present disclosure also generally relates to pharmaceutical compositions comprising the crystalline form(s), as well of methods of using the crystalline form(s) in the treatment of HIV and/or AIDS, and methods for obtaining such crystalline form(s). Compound (I) is 1-benzoyl-4-[2-[4-methoxy-7-(3-methyl-1H-1,2,4-triazol-1-yl)-1-[(phosphonooxy)methyl]-1H-pyrrolo[2,3-c]pyridin-3-yl]-1,2-dioxoethyl]-piperazine. Compound (I) herein and is described by Formula (I):

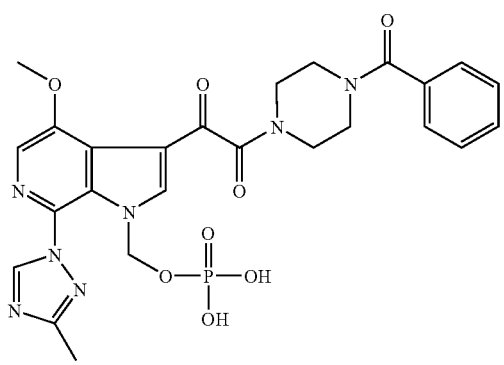

(I)

DEFINITIONS

As used herein "polymorph" refers to crystalline forms having the same chemical composition but different spatial arrangements of the molecules, atoms, and/or ions forming the crystal.

As used herein "solvate" refers to a crystalline form of a molecule, atom, and/or ions that further comprises molecules of a solvent or solvents incorporated into the crystalline lattice structure. The solvent molecules in the solvate may be present in a regular arrangement and/or a non-ordered arrangement. The solvate may comprise either a stoichiometric or nonstoichiometric amount of the solvent molecules. For example, a solvate with a nonstoichiometric amount of solvent molecules may result from partial loss of solvent from the solvate. Solvates may occur as dimers or oligomers comprising more than one molecule or Compound (I) within the crystalline lattice structure.

As used herein "amorphous" refers to a solid form of a molecule, atom, and/or ions that is not crystalline. An amorphous solid does not display a definitive X-ray diffraction pattern.

As used herein, "substantially pure," when used in reference to a crystalline form, means a compound having a purity greater than 90 weight %, including greater than 90, 91, 92, 93, 94, 95, 96, 97, 98, and 99 weight %, and also including equal to about 100 weight % of Compound (I), based on the weight of the compound. The remaining material comprises other form(s) of the compound, and/or reaction impurities and/or processing impurities arising from its preparation. For example, a crystalline form of Compound (I) may be deemed substantially pure in that it has a purity greater than 90 weight %, as measured by means that are at this time known and generally accepted in the art, where the remaining less than 10 weight % of material comprises other form(s) of Compound (I) and/or reaction impurities and/or processing impurities.

The term "pharmaceutically acceptable", as used herein, refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. In certain preferred embodiments, Compound (I) or each of its salts or solvates is in substantially pure form.

The term "substantially in accordance", as used herein, means one skilled in the art would considered to be the same, when taken into account variables such as instrumentation limitation, and instrumentation variation, etc.

The term "substantially pure crystal", as used herein, refers to samples of crystalline forms provided with substantially pure phase homogeneity, indicating the presence of a dominant amount of a single polymorph and optionally minor amounts of one or more other polymorphs. The presence of more than one polymorph in a sample may be determined by techniques such as powder x-ray diffraction (PXRD) or solid state nuclear magnetic resonance spectroscopy. For example, the presence of extra peaks in the comparison of an experimentally measured PXRD pattern with a simulated PXRD pattern may indicate more than one polymorph in the sample. The simulated PXRDPXRD may be calculated from single crystal x-ray data. see Smith, D. K., "*A FORTRAN Program for Calculating X-Ray Powder Diffraction Patterns,*" Lawrence Radiation Laboratory, Livermore, Calif., UCRL-7196 (April 1963).

The term "slurry", as used herein, means a saturated solution of the compound, which may also contain an additional amount of the compound to afford a heterogeneous mixture of the compound and a solvent at a given temperature.

"Therapeutically effective amount" is intended to include an amount of the crystalline forms of Compound (I) that is effective when administered alone or in combination to treat HIV and AIDS. The crystalline forms of Compound (I) and pharmaceutical compositions thereof may be useful in treating HIV or AIDS. If Compound (I) is used in combination with another medication, the combination of compounds described herein may result in a synergistic combination. Synergy, as described for example by Chou and Talalay, *Adv. Enzyme Regul.* 1984, 22, 27-55, occurs when the effect of the compounds when administered in combination is greater than the additive effect of the compounds when administered alone as a single agent.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis of Compound (I):

Compound (I) may be prepared using methods well known to the skilled artisan of organic synthesis, as well as methods taught in commonly owned U.S. non-provisional patent application Ser. No. 11/066,745 (filed Feb. 25, 2005) which is incorporated by reference herein in its entirety.

General Preparation of Crystalline Materials:

Procedures for the preparation of crystalline forms are known in the art. The crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in *Solid-State Chemistry of Drugs*, S. R. Byrn, R. R. Pfeiffer, and J. G. Stowell, $2^{nd}$ Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

Suitable solvents for preparing crystals include polar and nonpolar solvents. Examples of solvents for crystallization include, for example, toluene, n-pentane, n-hexane, n-heptane, n-octane, n-decane, n-dodecane, diethyl ether, methyl tertiary-butyl ether, triethylamine, diisopropyl ether, dibutylether, 1,4-dioxane, tetrahydrofuran, chloroform, 1,1-dichloroethane, ethyl acetate, 1,2-dichloroethane, 1,2-dibromoethane, dichloromethane, butyl ethanoate, 1-butanol, 2-methyl-2-propanol, 1-propanol, 1-octanol, ethanol, methyl ethyl ketone, acetone, cyclohexanone, 2-hexanone, cyclopentanone, 2-heptanone, 4-methyl-2-pentanone, acetonitrile, butanenitrile, ethylene glycol, methanol, diethylamine, glycerol, water, methyl acetate, isopropyl acetate, butyl acetate, t-butyl acetate, hexachloroacetone, 2-butanol, t-butyl alcohol, diethylene glycol, 1-, 2-, or 3-pentanol, 2-methyl-1-propanol, and 2-butanol.

In one method to prepare crystals, a compound is suspended and/or stirred in a suitable solvent to afford a slurry, which may be heated to promote dissolution.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, *Chemical Engineering Science,* 1971,26, 369-377. In general, seeds of small size are needed to control effectively the growth of crystals in the batch. Seed of small size may be generated by sieving, milling, or micronizing of large crystals, or by microcrystallization of solutions. Care should be taken that milling or micronizing of crystals does not result in any change in crystallinity form the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, differential scanning calorimetry, x-ray powder diffraction, or the like, to assure formation of the preferred crystalline form of the product. The resulting crystalline form is typically produced in an amount of greater than about 70 weight % isolated yield, preferably greater than 90 weight % isolated yield, based on the weight of the compound originally employed in the crystallization procedure. The product may be comilled or passed through a mesh screen to delump the product, if necessary.

Crystalline forms may be prepared directly from the reaction medium of the final process for preparing Compound (I). This may be achieved, for example, by employing in the final process step a solvent or a mixture of solvents from which Compound (I) may be crystallized. Alternatively, crystalline forms may be obtained by distillation or solvent addition techniques. Suitable solvents for this purpose include, for example, the aforementioned nonpolar solvents and polar solvents, including protic polar solvents such as alcohols, and aprotic polar solvents such as ketones.

Characterization:

The crystalline forms of Compound (I), its salts and solvates can be characterized by a number of methods, including but not limited to, Powder X-Ray diffraction (PXRD), simulated powder X-ray patterns (Yin. S.; Scaringe, R. P.; DiMarco, J.; Galella, M. and Gougoutas, J. Z., *American Pharmaceutical Review,* 2003, 6, 2, 80), Differential scanning calorimetry (DSC) experiments, Solid-state C-13 NMR measurements, (W. L. Earl and D. L. VanderHart, *J. Magn. Reson.,* 1982, 48, 35-54), Raman spectroscopy, Infra-red spectroscopy, Moisture sorption isotherms (VTI—variable temperature isotherms), and hot stage techniques.

The forms may be characterized and distinguished using single crystal x-ray diffraction, which is based on unit cell measurements of a single crystal of a particular form at a fixed analytical temperature. A detailed description of unit cells is provided in Stout & Jensen, X-Ray Structure Determination: A Practical Guide, Macmillan Co., New York (1968), Chapter 3, which is herein incorporated by reference. Alternatively, the unique arrangement of atoms in spatial relation within the crystalline lattice may be characterized according to the observed fractional atomic coordinates. Another means of characterizing the crystalline structure is by powder x-ray diffraction analysis in which the diffraction profile is compared to a simulated profile representing pure powder material, both run at the same analytical temperature, and measurements for the subject form characterized as a series of $2\theta$ values.

One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about 5% or less, and such degree of measurement error should be taken into account as pertaining to the aforementioned diffraction angles. Consequently, it is to be understood that the crystal forms of the instant invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

Likewise, it is to be understood that any crystal forms that provide differential scanning calorimetry (DSC), thermogravimetric analysis (TGA), and/or moisture sorption isotherms patterns substantially identical to those disclosed in the accompanying Figures fall within the scope of the present invention. The ability to ascertain substantial identities of these patterns is within the purview of one of ordinary skill in the art.

Utility:

Crystalline forms of Compound (I), its salts and solvates, alone or in combination with other compounds, can be used to treat AIDS and/or HIV infection.

The crystalline forms of the invention may be formulated with one or more excipients or other materials to provide formulations suitable for the treatment of the indications identified above.

The crystalline forms of the present invention may be administered by various routes, and can be dissolved in various solvents prior to administration.

In accordance with the present invention there is further provided a method of treating and a pharmaceutical composition for treating viral infections such as HIV infection and AIDS. The treatment involves administering to a patient in need of such treatment a pharmaceutical composition comprising a pharmaceutical carrier and a therapeutically-effective amount of a crystalline form of the present disclosure.

The pharmaceutical composition may be in the form of orally-administrable suspensions or tablets; nasal sprays, sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

Compound (I) may be present in the novel crystalline forms as the neat form, solvate and/or hydrate. A wide variety of solvents may be employed in the preparation of the solvates of Compound (I). Preferred solvents include, for example, polar solvents, including polar protic and polar aprotic solvents. In preferred form, the solvent employed in the preparation include, for example, DMF or acetone, preferably acetone. The ratio of Compound (I) to solvent in the solvates may vary and depends, for example, on the particular solvent selected and the methods for preparing the solvates. Preferably, the solvates are monosolvates, hemisolvates, non-stoichiometric or disolvates.

Abbreviations:

The following abbreviations, most of which are conventional abbreviations well known to those skilled in the art, are used throughout the description of the invention and the examples. Some of the abbreviations used are as follows:

| | | |
|---|---|---|
| h | = | hour(s) |
| rt | = | room temperature |
| mol | = | mole(s) |
| mmol | = | millimole(s) |
| g | = | gram(s) |
| mg | = | milligram(s) |
| mL | = | milliliter(s) |
| TFA | = | Trifluoroacetic Acid |
| DCE | = | 1,2-Dichloroethane |
| CH2C12 | = | Dichloromethane |
| TPAP | = | tetrapropylammonium perruthenate |
| THF | = | Tetrahydofuran |
| DEPBT | = | 3-(Diethoxyphosphoryloxy)-1,2,3-benzotriazin-4(3H)-one |
| DMAP | = | 4-dimethylaminopyridine |
| P-EDC | = | Polymer supported 1-(3-dimethylaminopropyl)-3-ethylcarbodiimide |
| EDC | = | 1-(3-dimethylaminopropyl)-3-ethylcarbodiimide |
| DMF | = | N,N-dimethylformamide |
| Hunig's Base | = | N,N-Diisopropylethylamine |
| mCPBA | = | meta-Chloroperbenzoic Acid |
| azaindole | = | 1H-Pyrrolo-pyridine |
| 4-azaindole | = | 1H-pyrrolo[3,2-]pyridine |
| 5-azaindole | = | 1H-Pyrrolo[3,2-c]pyridine |
| 6-azaindole | = | 1H-pyrrolo[2,3-c]pyridine |
| 7-azaindole | = | 1H-Pyrrolo[2,3-b]pyridine |
| PMB | = | 4-Methoxybenzyl |
| DDQ | = | 2, 3-Dichloro-5, 6-dicyano-1, 4-benzoquinone |
| OTf | = | Trifluoromethanesulfonoxy |
| NMM | = | 4-Methylmorpholine |
| PIP-COPh | = | 1-Benzoylpiperazine |
| NaHMDS | = | Sodium hexamethyldisilazide |
| EDAC | = | 1-(3-Dimethylaminopropyl)-3-ethylcarbodiimide |
| TMS | = | Trimethylsilyl |
| DCM | = | Dichloromethane |
| DCE | = | Dichloroethane |
| MeOH | = | Methanol |
| THF | = | Tetrahrdrofuran |
| EtOAc | = | Ethyl Acetate |
| LDA | = | Lithium diisopropylamide |
| TMP-Li | = | 2,2,6,6-tetramethylpiperidinyl lithium |
| DME | = | Dimethoxyethane |
| DIBALH | = | Diisobutylaluminum hydride |
| HOBT | = | 1-hydroxybenzotriazole |
| CBZ | = | Benzyloxycarbonyl |
| PCC | = | Pyridinium chlorochromate |
| Me | = | Methyl |
| Ph | = | Phenyl |

The crystalline materials of Compound (I) described herein may be formulated into pharmaceutical compositions and/or employed in therapeutic and/or prophylactic methods. These methods include, but are not limited to, the administration of the crystalline compound (I), alone or in combination with one or more other pharmaceutically active agents, including agents that may be useful in the treatment of the disorders mentioned herein.

The methods preferably comprise administering to a patient a pharmaceutically effective amount of the novel crystals of the present invention, preferably in combination with one or more pharmaceutically acceptable carriers and/or excipients. The relative proportions of active ingredient and carrier and/or excipient may be determined, for example, by the solubility and chemical nature of the materials, chosen route of administration and standard pharmaceutical practice.

The crystalline forms of Compound (I) may be administered to a patient in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They may be administered alone, but generally will be administered with a pharmaceutical carrier selected on the basis of the chosen route of administration and standard pharmaceutical practice.

The dosage regimen for the crystalline forms of Compound (I) will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder. Obviously, several unit dosage forms may be administered at about the same time. The dosage of the crystalline form of Compound (I) that will be most suitable for prophylaxis or treatment may vary with the form of administration, the particular crystalline form of the compound chosen and the physiological characteristics of the particular patient under treatment. Broadly, small dosages may be used initially and, if necessary, increased by small increments until the desired effect under the circumstances is reached.

By way of general guidance, in the adult, suitable doses may range from about 0.001 to about 1000 mg/Kg body weight, and all combinations and subcombinations of ranges and specific doses therein. Preferred doses may be from about 0.01 to about 100 mg/kg body weight per day by inhalation, preferably 0.1 to 70, more preferably 0.5 to 20 mg/Kg body weight per day by oral administration, and from about 0.01 to about 50, preferably 0.01 to 10 mg/Kg body weight per day by intravenous administration. In each particular case, the doses may be determined in accordance with the factors distinctive to the subject to be treated, such as age, weight, general state of health and other characteristics which can influence the efficacy of the medicinal product. The crystalline forms of Compound (I) may be administered in a single daily dose, or the total daily dosage may be administered in divided doses of two, three, or four times daily.

For oral administration in solid form such as a tablet or capsule, the crystalline forms of Compound (I) can be combined with a non-toxic, pharmaceutically acceptable inert carrier, such as lactose, starch, sucrose, glucose, methylcellulose, magnesium stearate, dicalcium phosphate, calcium sulfate, mannitol, sorbitol and the like.

Preferably, in addition to the active ingredient, solid dosage forms may contain a number of additional ingredients referred to herein as "excipients". These excipients include among others diluents, binders, lubricants, glidants and disintegrants. Coloring agents may also be incorporated. "Diluents", as used herein, are agents which impart bulk to the formulation to make a tablet a practical size for compression. Examples of diluents are lactose and cellulose. "Binders", as used herein, are agents used to impart cohesive qualities to the powered material to help ensure the tablet will remain intact after compression, as well as improving the free-flowing qualities of the powder. Examples of typical binders are lactose, starch and various sugars. "Lubricants", as used herein, have several functions including preventing the adhesion of the tablets to the compression equipment and improving the flow of the granulation prior to compression or encapsulation. Lubricants are in most cases hydrophobic materials. Excessive use of lubricants is undesired, however, as it may result in a formulation with reduced disintegration and/or delayed dissolution of the drug substance. "Glidants", as used herein, refer to substances which may improve the flow characteristics of the granulation material. Examples of glidants include talc and colloidal silicon dioxide. "Disintegrants", as used herein, are substances or a mixture of substances added to a formulation to facilitate the breakup or disintegration of the solid dosage form after administration. Materials that may serve as disintegrants include starches, clays, celluloses, algins, gums and cross-linked polymers. A group of disintegrants referred to as "super-disintegrants" generally are used at a low level in the solid dosage form, typically 1% to 10% by weight relative to the total weight of the dosage unit. Croscarmelose, crospovidone and sodium starch glycolate represent examples of a cross-linked cellulose, a cross-linked polymer and a cross-linked starch, respectively. Sodium starch glycolate swells seven- to twelve-fold in less than 30 seconds effectively disintegrating the granulations that contain it.

The disintegrant preferably used in the present invention is selected from the group comprising modified starches, croscarmallose sodium, carboxymethylcellulose calcium and crospovidone. A more preferred disintegrant in the present invention is a modified starch such as sodium starch glycolate.

Preferred carriers include capsules or compressed tablets which contain the solid pharmaceutical dosage forms described herein. Preferred capsule or compressed tablet forms generally comprise a therapeutically effective amount of the crystalline forms of Compound (I) and one or more disintegrants in an amount greater than about 10% by weight relative to the total weight of the contents of the capsule or the total weight of the tablet.

Preferred capsule formulations may contain the crystalline forms of Compound (I) in an amount from about 5 to about 1000 mg per capsule. Preferred compressed tablet formulations contain the crystalline forms of Compound (I) in an amount from about 5 mg to about 800 mg per tablet. More preferred formulations contain about 50 to about 200 mg per capsule or compressed tablet. Preferably, the capsule or compressed tablet pharmaceutical dosage form comprises a therapeutically effective amount of a crystalline form of Compound (I); a surfactant; a disintegrant; a binder; a lubricant; and optionally additional pharmaceutically acceptable excipients such as diluents, glidants and the like; wherein the disintegrant is selected from modified starches; croscarmallose sodium, carboxymethylcellulose calcium and crospovidone.

For oral administration in liquid form, the crystalline forms of Compound (I) can be combined with any oral, non-toxic pharmaceutically acceptable inert carrier such as ethanol, glycerol, water and the like. The liquid composition may contain a sweetening agent which to make the compositions more palatable. The sweetening agent can be selected from a sugar such as sucrose, mannitol, sorbitol, xylitol, lactose, etc. or a sugar substitute such as cyclamate, saccharin, aspartame, etc. If sugar substitutes are selected as the sweetening agent the amount employed in the compositions of the invention will be substantially less than if sugars are employed. Taking this into account, the amount of sweetening agent may range from about 0.1 to about 50% by weight, and all combinations and subcombinations of ranges and specific amounts therein. Preferred amounts range from about 0.5 to about 30% by weight.

The more preferred sweetening agents are the sugars and particularly sucrose. The particle size of the powdered sucrose used has been found to have a significant influence in the physical appearance of the finished composition and its ultimate acceptance for taste. The preferred particle size of the sucrose component when used is in the range of from 200 to less than 325 mesh US Standard Screen, and all combinations and subcombinations of ranges and specific particle sizes therein.

Sterile injectable solutions may be prepared by incorporating the crystalline forms of Compound (I) in the required amounts, in the appropriate solvent, with various of the other ingredients enumerated herein, as required, followed by filtered sterilization. Generally, dispersions may be prepared by incorporating the sterilized active ingredient into a sterile vehicle which contains the dispersion medium and any other required ingredients. In the case of sterile powders for the preparation of sterile injectable solutions, the preferred methods of preparation may include vacuum drying and the freeze drying technique which may yield a powder of the active ingredient, plus any additional desired ingredient from the previously sterile-filtered solution thereof.

As would be apparent to a person of ordinary skill in the art, once armed with the teachings of the present disclosure, when dissolved, Compound (I) loses its crystalline structure, and is therefore considered to be a solution of Compound (I). All forms of the present invention, however, may be used for the preparation of liquid formulations in which Compound (I) may be, for example, dissolved or suspended. In addition, the crystalline forms of Compound (I) may be incorporated into solid formulations.

The liquid compositions may also contain other components routinely utilized in formulating pharmaceutical compositions. One example of such components is lecithin. Its use in compositions of the invention as an emulsifying agent in the range of from 0.05 to 1% by weight, and all combinations and subcombinations of ranges and specific amounts therein. More preferably, emulsifying agents may be employed in an amount of from about 0.1 to about 0.5% by weight. Other examples of components that may be used are antimicrobial preservatives, such as benzoic acid or parabens; suspending agents, such as colloidal silicon dioxide; antioxidants; topical oral anesthetics; flavoring agents; and colorants.

The selection of such optional components and their level of use in the compositions of the invention is within the level of skill in the art and will be even better appreciated from the working examples provided hereinafter.

The crystalline forms of Compound (I) may also be coupled with soluble polymers as targetable drug carriers. Such polymers can include polyvinylpyrrolidine pyran copolymer, polyhydroxypropylmethacrylamide-phenol, polyhydroxyethyl-aspartamidephenol or polyethylene oxide-polylysine substituted with palmitoyl residues. Gelatin capsules of the crystalline forms of Compound (I) may contain the crystalline Compound (I) and the liquid or solid compositions described herein. Gelatin capsules may also contain powdered carriers such as lactose, starch, cellulose derivatives, magnesium stearate, stearic acid and the like. Similar diluents can be used to make compressed tablets. Both tablets and capsules can be manufactured as sustained release products to provide for continuous release of medication over a period of hours. Tablets can be sugar coated or film coated to mask any unpleasant taste and to protect the tablet from the atmosphere or enteric coated for selective disintegration in the gastrointestinal track.

In general, water, a suitable oil, saline, aqueous dextrose (glucose), and related sugar solutions and glycols, such as propylene glycol or polyethylene glycols are suitable carriers for parenteral solutions. Solutions for parenteral solutions are prepared by dissolving the crystalline Efavirenz in the carrier and, if necessary, adding buffering substances. Anti-oxidizing agents such as sodium bisulfite, sodium sulfite, or ascorbic acid either alone or combined, are suitable stabilizing agents. Citric acid and its salts and sodium EDTA may also be employed. Parenteral solutions may also contain preservatives, such as benzalkonium chloride, methyl- or propyl-paraben and chlorobutanol.

Suitable pharmaceutical carriers are described in Remington's Pharmaceutical Sciences, Mack Publishing Co., the disclosures of which are hereby incorporated herein by reference, in their entireties.

The preferred crystalline form of Compound (I) may serve as component (a) of this invention and can independently be in any dosage form, such as those described above, and can also be administered in various combinations, as described above. In the following description component (b) is to be understood to represent one or more agents as described herein suitable for combination therapy.

Pharmaceutical kits which may be useful for the treatment of various disorders, and which comprise a therapeutically effective amount of a pharmaceutical composition comprising a novel form of Compound (I) in one or more sterile containers, are also within the ambit of the present invention. The kits may further comprise conventional pharmaceutical kit components which will be readily apparent to those skilled in the art, once armed with the present disclosure. Sterilization of the container may be carried out using conventional sterilization methodology well known to those skilled in the art.

Form 01-H2-1 of Compound (I)

Form 01-H2-1 of Compound (I) is a di-hydrate with empirical formula $C_{25}H_{26}N_7O_8P_1 \cdot 2H_2O$ The single crystal of Form 01-H2-1 is characterized in Table 1.

Each of the atoms (except H) in Form 01-H2-1 is labeled according to FIG. 3. The fractional atomic coordinates of are listed in Table 2.

Form 02-SA-1 of Compound (I)

Form 02-SA-1 of Compound (I) is a hemiethanolate octahydrate of di-sodium salt with empirical formula of $C_{25}H_{24}N_7O_8P_1Na_2 \cdot 8H_2O \cdot 0.5C_2H_5OH$.

The single crystal of Form 02-SA-1 is characterized in Table 3.

Each of the atoms (except H) in Form 02-SA-1 is labeled according to FIG. 5. The fractional atomic coordinates of are listed in Table 4.

Form 03-E.5-1 of Compound (I)

Form 03-E.5-1 of Compound (I) is a hemiethanolate of mono-TRIS salt with empirical formula of $C_{25}H_{26}N_7O_8P_1 \cdot C_4H_{11}N_1O_3 \cdot 0.5C_2H_5OH$.

The single crystal of Form 03-E.5-1 is characterized in Table 5.

Each of the atoms (except H) in Form 03-E.5-1 is labeled according to FIG. 8. The fractional atomic coordinates of are listed in Table 6.

Form 03-SA-2 of Compound (I)

Form 03-SA-2 of Compound (I) is a hemiacetonate hemihydrate of mono-TRIS salt with empirical formula of $C_{25}H_{26}N_7O_8P_1 \cdot C_4H_{11}N_1O_3 \cdot 0.5H_2O \cdot 0.5C_3H_6O$.

The single crystal of Form 03-SA-2 is characterized in Table 7.

Each of the atoms (except H) in Form 03-SA-2 is labeled according to FIG. 11. The fractional atomic coordinates of are listed in Table 8.

Form 03-DSA-2 of Compound (I)

Form 03-DSA-2 of Compound (I) is a mono-TRIS salt which is a dehydrated and desolvated formo of Form 03-SA-2.

TABLE 1

Single Crystal Characterization of Form 01-H2-1

| | |
|---|---|
| Temperature | 293(2) K. |
| Wavelength | 1.54178 Å |
| Crystal system, space group | Monoclinic, P2(1)/c |
| Unit cell dimensions | a = 17.2174(18) Å |
| | α = 90° |
| | b = 18.1242(19) Å |
| | β = 105.191(4)° |
| | c = 9.3705(9) Å |
| | γ = 90° |
| Volume | 2821.9(5) Å$^3$ |
| Z, Calculated density | 4, 1.458 Mg/m$^3$ |
| Absorption coefficient | 1.474 mm$^{-1}$ |
| F(000) | 1296 |
| Crystal size | 0.18 × 0.15 × 0.01 mm |
| θ range for data collection | 2.66 to 39.60° |
| Limiting indices | -13 <= h <= 13, -13 <= k <= 14, -7 <= l <= 7 |
| Reflections collected/unique | 4367/1423 [R(int) = 0.1318] |
| Completeness to θ = 39.60 | 85.5% |
| Absorption correction | SADABS |
| Max. and min. transmission | 1.000 and 0.557 |
| Refinement method | Full-matrix least-squares on F$^2$ |
| Data/restraints/parameters | 1423/0/379 |
| Goodness-of-fit on F$^2$ | 1.066 |
| Final R indices [I > 2σ(I)] | R1 = 0.0806, wR2 = 0.1864 |
| R indices (all data) | R1 = 0.1146, wR2 = 0.2028 |
| Largest diff. peak and hole | 0.246 and -0.265 e.Å$^{-3}$ |

TABLE 2

Atomic coordinates (×10$^4$) and equivalent isotropic displacement parameters (A$^2$ × 10$^3$) for Form 01-H2-1. U(eq) is defined as one third of the trace of the orthogonalized Uij tensor.

| | x | y | z | U(eq) |
|---|---|---|---|---|
| P(1) | 8692(3) | 2452(3) | 886(5) | 58(2) |
| O(1) | 7863(7) | 2046(8) | 691(11) | 85(4) |
| O(2) | 9208(6) | 2345(5) | 2464(10) | 74(3) |
| O(3) | 9134(6) | 2119(5) | -166(11) | 85(4) |
| O(4) | 8450(5) | 3230(6) | 438(9) | 73(3) |
| O(5) | 4159(9) | 1141(5) | 590(10) | 57(3) |
| O(6) | 5716(9) | 2151(6) | 4721(15) | 81(5) |
| O(7) | 4141(9) | 2605(7) | 2202(13) | 82(5) |
| O(8) | 2990(8) | -173(7) | 6428(13) | 82(5) |

TABLE 2-continued

Atomic coordinates (×10$^4$) and equivalent isotropic displacement parameters (A$^2$ × 10$^3$) for Form 01-H2-1. U(eq) is defined as one third of the trace of the orthogonalized Uij tensor.

| | x | y | z | U(eq) |
|---|---|---|---|---|
| N(1) | 6889(16) | 1504(10) | 1580(30) | 55(6) |
| N(2) | 5481(18) | 686(7) | -1765(18) | 62(6) |
| N(3) | 6844(14) | 911(12) | -1530(30) | 50(4) |
| N(4) | 7493(18) | 443(9) | -982(15) | 59(5) |
| N(5) | 7666(15) | 1106(13) | -2890(20) | 57(6) |
| N(6) | 3989(13) | 1677(11) | 3686(18) | 62(5) |
| N(7) | 2982(11) | 670(9) | 4620(20) | 61(5) |
| C(1) | 6560(20) | 1757(8) | 2710(20) | 49(6) |
| C(2) | 6280(20) | 1218(13) | 520(50) | 54(11) |
| C(3) | 6160(20) | 942(11) | -950(30) | 58(8) |
| C(4) | 4815(13) | 753(9) | -1190(30) | 54(6) |
| C(5) | 4880(20) | 1092(11) | 190(30) | 56(8) |
| C(6) | 5580(20) | 1328(11) | 1000(40) | 64(13) |
| C(7) | 5780(20) | 1689(10) | 2440(30) | 49(8) |
| C(8) | 7729(15) | 1491(9) | 1654(17) | 61(6) |
| C(9) | 6967(18) | 1280(10) | -2670(30) | 57(7) |
| C(10) | 7994(15) | 588(13) | -1820(40) | 63(7) |
| C(11) | 8805(12) | 276(9) | -1620(20) | 95(6) |
| C(12) | 3391(11) | 1028(9) | -411(18) | 82(6) |
| C(13) | 5320(20) | 1956(9) | 3520(30) | 53(6) |
| C(14) | 4470(20) | 2089(14) | 3030(20) | 63(7) |
| C(15) | 3197(13) | 1884(8) | 3658(16) | 56(5) |
| C(16) | 2626(10) | 1235(11) | 3533(16) | 71(7) |
| C(17) | 3762(14) | 410(8) | 4532(17) | 63(5) |
| C(18) | 4348(10) | 1045(10) | 4757(15) | 57(5) |
| C(19) | 2655(14) | 360(13) | 5690(30) | 55(6) |
| C(20) | 1920(20) | 614(14) | 5970(20) | 80(10) |
| C(21) | 1278(19) | 186(12) | 6130(20) | 95(9) |
| C(22) | 629(17) | 530(20) | 6570(30) | 154(13) |
| C(23) | 630(20) | 1270(20) | 6770(30) | 153(12) |
| C(24) | 1240(20) | 1703(14) | 6640(30) | 124(11) |
| C(25) | 1878(12) | 1340(20) | 6199(19) | 96(10) |
| O(1W) | 10482(16) | 1379(15) | 2580(30) | 375(14) |
| O(2W) | 11290(90) | 1740(100) | 410(180) | 340(80) |

TABLE 3

Single Crystal Characterization of Form 02-SA-1

| | |
|---|---|
| Temperature | 173(2) K. |
| Wavelength | 1.54178 Å |
| Crystal system, space group | Triclinic, P-1 |
| Unit cell dimensions | a = 6.4392(12) Å |
| | α = 99.082(11)° |
| | b = 13.349(2) Å |
| | β = 95.975(12)° |
| | c = 21.041(4) Å |
| | γ = 90.207(12)° |
| Volume | 1775.9(6) Å$^3$ |
| Z, Calculated density | 2, 1.486 Mg/m$^3$ |
| Absorption coefficient | 1.661 mm$^{-1}$ |
| F(000) | 834 |
| Crystal size | 0.62 × 0.03 × 0.01 mm |
| θ range for data collection | 2.14 to 65.49° |
| Limiting indices | -7 <= h <= 7, -14 <= k <= 15, -22 <= l <= 24 |
| Reflections collected/unique | 9051/5226 [R(int) = 0.0983] |
| Completeness to θ = 65.49 | 85.1% |
| Absorption correction | SADABS |
| Max. and min. transmission | 1.000 and 0.749 |
| Refinement method | Full-matrix least-squares on F$^2$ |
| Data/restraints/parameters | 5226/0/481 |
| Goodness-of-fit on F$^2$ | 1.144 |
| Final R indices [I > 2σ(I)] | R1 = 0.1086, wR2 = 0.2554 |
| R indices (all data) | R1 = 0.1373, wR2 = 0.2674 |
| Extinction coefficient | 0.0007(3) |
| Largest diff. peak and hole | 0.604 and -0.524 e.Å$^{-3}$ |

TABLE 4

Atomic coordinates (×10$^4$) and equivalent isotropic displacement parameters (A$^2$ × 10$^3$) for Form 02-SA-1. U(eq) is defined as one third of the trace of the orthogonalized Uij tensor.

|        | x        | y       | z       | U(eq)  |
|--------|----------|---------|---------|--------|
| P(1)   | −4237(3) | 7620(2) | 623(1)  | 16(1)  |
| O(1)   | −4989(9) | 8163(4) | 1326(3) | 25(1)  |
| O(2)   | −5171(8) | 6554(4) | 520(3)  | 22(1)  |
| O(3)   | −5197(8) | 8294(4) | 166(3)  | 22(1)  |
| O(4)   | −1871(8) | 7657(4) | 690(3)  | 25(1)  |
| O(5)   | 2971(9)  | 6724(5) | 3257(3) | 37(2)  |
| O(6)   | −443(9)  | 4328(5) | 1972(3) | 34(2)  |
| O(7)   | −623(10) | 5024(5) | 3498(3) | 34(2)  |
| O(8)   | 8772(10) | 2512(5) | 2958(3) | 40(2)  |
| N(1)   | −3283(10)| 7198(5) | 2088(3) | 22(2)  |
| N(2)   | 83(11)   | 9077(6) | 3216(4) | 33(2)  |
| N(3)   | −2903(11)| 9486(5) | 2603(4) | 25(2)  |
| N(4)   | −4611(12)| 9754(5) | 2928(4) | 31(2)  |
| N(5)   | −4533(12)| 10601(5)| 2080(4) | 31(2)  |
| N(6)   | 2561(12) | 4517(6) | 3211(4) | 34(2)  |
| N(7)   | 5741(12) | 3115(6) | 3293(4) | 32(2)  |
| C(1)   | −2782(13)| 6193(6) | 1988(4) | 25(2)  |
| C(2)   | −1727(12)| 7723(6) | 2524(4) | 21(2)  |
| C(3)   | −1474(13)| 8732(6) | 2781(4) | 25(2)  |
| C(4)   | 1524(14) | 8414(7) | 3380(5) | 33(2)  |
| C(5)   | 1479(14) | 7403(7) | 3130(5) | 29(2)  |
| C(6)   | −279(12) | 7022(6) | 2704(4) | 24(2)  |
| C(7)   | −951(13) | 6043(6) | 2361(4) | 24(2)  |
| C(8)   | −5253(12)| 7582(6) | 1812(4) | 22(2)  |
| C(9)   | −2903(13)| 10008(6)| 2114(4) | 25(2)  |
| C(10)  | −5520(14)| 10418(6)| 2588(4) | 27(2)  |
| C(11)  | −7555(15)| 10885(6)| 2743(5) | 39(3)  |
| C(12)  | 4739(15) | 7096(8) | 3710(6) | 44(3)  |
| C(13)  | −149(13) | 5019(7) | 2410(5) | 27(2)  |
| C(14)  | 656(14)  | 4851(7) | 3085(5) | 29(2)  |
| C(15)  | 3338(15) | 4299(7) | 3846(5) | 36(2)  |
| C(16)  | 4190(14) | 3229(8) | 3772(5) | 36(2)  |
| C(17)  | 4981(14) | 3376(7) | 2664(5) | 32(2)  |
| C(18)  | 4121(14) | 4434(7) | 2745(5) | 31(2)  |
| C(19)  | 7652(14) | 2726(7) | 3400(5) | 33(2)  |
| C(20)  | 8481(14) | 2595(7) | 4058(5) | 32(2)  |
| C(21)  | 8767(16) | 3406(8) | 4583(5) | 39(2)  |
| C(22)  | 9755(17) | 3241(10)| 5166(6) | 54(3)  |
| C(23)  | 10388(18)| 2291(11)| 5258(6) | 59(4)  |
| C(24)  | 10121(18)| 1497(10)| 4760(6) | 54(3)  |
| C(25)  | 9200(16) | 1651(8) | 4168(6) | 42(3)  |
| Na(1)  | −27(5)   | 4278(2) | 751(2)  | 32(1)  |
| Na(2)  | 584(5)   | 824(2)  | 799(2)  | 27(1)  |
| O(1W)  | −582(9)  | 2420(4) | 342(3)  | 30(2)  |
| O(2W)  | 702(10)  | 5950(5) | 649(4)  | 41(2)  |
| O(3W)  | 3223(10) | 3816(5) | 1156(3) | 33(2)  |
| O(4W)  | −3536(9) | 4645(4) | 623(3)  | 27(1)  |
| O(5W)  | −2364(9) | 19(4)   | 135(3)  | 26(1)  |
| O(6W)  | 929(9)   | −739(4) | 1222(3) | 30(2)  |
| O(7W)  | 3859(9)  | 1718(4) | 1081(3) | 29(1)  |
| O(8W)  | −868(11) | 1918(5) | 1629(4) | 40(2)  |
| O(101) | −3944    | 9520    | 4308    | 48     |
| C(101) | −4921    | 10189   | 4691    | 79     |
| C(102) | −5079    | 9811    | 5309    | 79     |

TABLE 5

Single Crystal Characterization of Form 03-E.5-1

| Temperature | 293(2) K. |
|---|---|
| Wavelength | 1.54178 Å |
| Crystal system, space group | Monoclinic, C2/c |
| Unit cell dimensions | a = 35.594(2) Å |
| | α = 90° |
| | b = 6.2790(4) Å |
| | β = 97.080(3)° |
| | c = 30.6961(19) Å |
| | γ = 90° |
| Volume | 6808.1(7) Å$^3$ |
| Z, Calculated density | 8, 1.420 Mg/m$^3$ |
| Absorption coefficient | 1.349 mm$^{-1}$ |
| F (000) | 3064 |
| Crystal size | 0.62 × 0.02 × 0.01 mm |
| θ range for data collection | 2.50 to 60.58° |
| Limiting indices | −39 <= h <= 37, −6 <= k <= 6, −34 <= l <= 32 |
| Reflections collected/unique | 16059/4932 [R(int) = 0.0844] |
| Completeness to θ = 60.58 | 96.0% |
| Absorption correction | SADABS |
| Max. and min. transmission | 1.000 and 0.796 |
| Refinement method | Full-matrix least-squares on F$^2$ |
| Data/restraints/parameters | 4932/0/472 |
| Goodness-of-fit on F$^2$ | 0.955 |
| Final R indices [I > 2σ(I)] | R1 = 0.0619, wR2 = 0.1236 |
| R indices (all data) | R1 = 0.1245, wR2 = 0.1426 |
| Largest diff. peak and hole | 0.299 and −0.245 e.A$^{-3}$ |

TABLE 6

Atomic coordinates (×10$^4$) and equivalent isotropic displacement parameters (A$^2$ × 10$^3$) for Form 03-E.5-1. U(eq) is defined as one third of the trace of the orthogonalized Uij tensor.

|        | x       | y        | z       | U(eq)  |
|--------|---------|----------|---------|--------|
| P(1)   | 2596(1) | 6394(2)  | 2987(1) | 40(1)  |
| O(1)   | 2976(1) | 7325(4)  | 2829(1) | 44(1)  |
| O(2)   | 2545(1) | 7326(4)  | 3424(1) | 49(1)  |
| O(3)   | 2295(1) | 6805(4)  | 2618(1) | 49(1)  |
| O(4)   | 2670(1) | 3962(4)  | 3055(1) | 49(1)  |
| O(5)   | 4192(1) | 1209(5)  | 4004(1) | 54(1)  |
| O(6)   | 3534(1) | 5503(5)  | 4738(1) | 65(1)  |
| O(7)   | 4409(1) | 5226(5)  | 4729(1) | 61(1)  |
| O(8)   | 3768(1) | −3613(6) | 5844(1) | 96(1)  |
| N(1)   | 3483(1) | 6854(5)  | 3404(1) | 38(1)  |
| N(2)   | 3986(1) | 2708(6)  | 2844(1) | 52(1)  |
| N(3)   | 3667(1) | 5526(6)  | 2482(1) | 43(1)  |
| N(4)   | 3842(1) | 7331(7)  | 2362(1) | 59(1)  |
| N(5)   | 3364(1) | 6428(7)  | 1848(1) | 56(1)  |
| N(6)   | 4143(1) | 2180(5)  | 4952(1) | 45(1)  |
| N(7)   | 4070(1) | −758(6)  | 5621(1) | 46(1)  |
| C(1)   | 3483(1) | 6826(6)  | 3842(1) | 38(1)  |
| C(2)   | 3703(1) | 5168(7)  | 3281(1) | 36(1)  |
| C(3)   | 3787(1) | 4441(8)  | 2880(1) | 41(1)  |
| C(4)   | 4121(1) | 1637(7)  | 3212(1) | 51(1)  |
| C(5)   | 4061(1) | 2252(7)  | 3627(2) | 41(1)  |
| C(6)   | 3847(1) | 4108(7)  | 3670(1) | 36(1)  |
| C(7)   | 3705(1) | 5188(7)  | 4030(1) | 37(1)  |
| C(8)   | 3262(1) | 8359(7)  | 3107(1) | 46(1)  |
| C(9)   | 3383(1) | 5037(8)  | 2172(2) | 52(1)  |
| C(10)  | 3645(1) | 7796(8)  | 1981(2) | 58(1)  |
| C(11)  | 3740(2) | 9697(9)  | 1724(2) | 115(2) |
| C(12)  | 4433(1) | −573(7)  | 3969(2) | 63(2)  |
| C(13)  | 3761(1) | 4840(7)  | 4507(2) | 43(1)  |
| C(14)  | 4140(1) | 4025(8)  | 4732(1) | 45(1)  |
| C(15)  | 4480(1) | 1450(7)  | 5226(1) | 49(1)  |
| C(16)  | 4374(1) | 812(7)   | 5670(1) | 49(1)  |
| C(17)  | 3733(1) | −2(7)    | 5348(2) | 59(1)  |
| C(18)  | 3834(1) | 626(7)   | 4904(2) | 55(1)  |
| C(19)  | 4062(2) | −2603(9) | 5839(2) | 53(1)  |
| C(20)  | 4418(1) | −3458(7) | 6084(1) | 44(1)  |
| C(21)  | 4741(1) | −3755(7) | 5886(2) | 51(1)  |
| C(22)  | 5054(2) | −4692(8) | 6112(2) | 65(2)  |
| C(23)  | 5052(2) | −5317(8) | 6535(2) | 76(2)  |
| C(24)  | 4730(2) | −5082(8) | 6736(2) | 83(2)  |
| C(25)  | 4410(2) | −4182(8) | 6508(2) | 66(2)  |
| N(101) | 2345(1) | 1293(6)  | 3682(1) | 44(1)  |
| C(100) | 2381(1) | 1642(7)  | 4167(1) | 40(1)  |
| C(101) | 2762(1) | 720(7)   | 4368(2) | 55(1)  |
| O(101) | 3063(1) | 1335(6)  | 4132(1) | 65(1)  |

TABLE 6-continued

Atomic coordinates (×10⁴) and equivalent isotropic displacement parameters ($A^2 \times 10^3$) for Form 03-E.5-1. U(eq) is defined as one third of the trace of the orthogonalized Uij tensor.

| | x | y | z | U(eq) |
|---|---|---|---|---|
| C(102) | 2353(1) | 4024(7) | 4246(1) | 57(1) |
| O(102) | 2678(1) | 5114(5) | 4152(1) | 67(1) |
| C(103) | 2058(2) | 516(8) | 4341(2) | 73(2) |
| O(10A) | 1756(3) | 1422(14) | 4227(3) | 75(3) |
| O(10B) | 2000(3) | −1430(20) | 4230(4) | 92(4) |
| O(10C) | 2038(2) | 504(16) | 4742(4) | 59(6) |
| O(201) | 4628(2) | 8300(11) | 2632(2) | 79(2) |
| C(201) | 4808(10) | 10130(30) | 2382(19) | 125(11) |
| C(202) | 5201(10) | 10250(30) | 2474(18) | 125(11) |

TABLE 7

Single Crystal Characterization of Form 03-SA-2

| | |
|---|---|
| Temperature | 293(2) K. |
| Wavelength | 0.71073 Å |
| Crystal system, space group | Monoclinic, C2/c |
| Unit cell dimensions | a = 43.985(2) Å |
| | α = 90° |
| | b = 6.3142(3) Å |
| | β = 125.742(4)° |
| | c = 30.2438(17) Å |
| | γ = 90° |
| Volume | 6817.6(6) Å³ |
| Z, Calculated density | 8, 1.399 Mg/m³ |
| Absorption coefficient | 0.152 mm⁻¹ |
| F(000) | 3019 |
| Crystal size | 0.30 × 0.02 × 0.01 mm |
| θ range for data collection | 2.80 to 24.94° |
| Limiting indices | −52 <= h <= 51, −7 <= k <= 7, −35 <= l <= 35 |
| Reflections collected/unique | 18438/5934 [R(int) = 0.1655] |
| Completeness to θ = 24.94 | 99.2% |
| Absorption correction | None |
| Refinement method | Full-matrix least-squares on F² |
| Data/restraints/parameters | 5934/0/472 |
| Goodness-of-fit on F² | 1.006 |
| Final R indices [I > 2σ(I)] | R1 = 0.0718, wR2 = 0.1474 |
| R indices (all data) | R1 = 0.1697, wR2 = 0.1917 |
| Extinction coefficient | 0.0010(2) |
| Largest diff. peak and hole | 0.256 and −0.291 e.A³ |

TABLE 8

Atomic coordinates (×10⁴) and equivalent isotropic displacement parameters ($A^2 \times 10^3$) for Form 03-SA-2. U(eq) is defined as one third of the trace of the orthogonalized Uij tensor.

| | x | y | z | U(eq) |
|---|---|---|---|---|
| P(1) | 2400(1) | −1012(2) | 2897(1) | 45(1) |
| O(1) | 2024(1) | −1939(5) | 2360(1) | 49(1) |
| O(2) | 2448(1) | −1930(5) | 3390(1) | 54(1) |
| O(3) | 2702(1) | −1428(5) | 2826(1) | 53(1) |
| O(4) | 2324(1) | 1394(5) | 2883(1) | 53(1) |
| O(5) | 826(1) | 4216(6) | 2334(2) | 61(1) |
| O(6) | 1425(1) | −139(7) | 3709(2) | 78(1) |
| O(7) | 567(1) | 349(7) | 2788(2) | 80(1) |
| O(8) | 1221(1) | 8772(9) | 4661(2) | 108(2) |
| N(1) | 1519(1) | −1468(6) | 2434(2) | 46(1) |
| N(2) | 1038(1) | 2675(7) | 1370(2) | 55(1) |
| N(3) | 1357(1) | −156(7) | 1330(2) | 49(1) |
| N(4) | 1192(1) | −2003(8) | 1064(2) | 64(1) |
| N(5) | 1659(1) | −1090(8) | 996(2) | 61(1) |
| N(6) | 842(1) | 3250(7) | 3322(2) | 56(1) |
| N(7) | 909(1) | 6073(7) | 4090(2) | 55(1) |

TABLE 8-continued

Atomic coordinates (×10⁴) and equivalent isotropic displacement parameters ($A^2 \times 10^3$) for Form 03-SA-2. U(eq) is defined as one third of the trace of the orthogonalized Uij tensor.

| | x | y | z | U(eq) |
|---|---|---|---|---|
| C(1) | 1507(1) | −1409(8) | 2876(2) | 48(1) |
| C(2) | 1306(1) | 222(8) | 2098(2) | 45(1) |
| C(3) | 1232(1) | 939(8) | 1609(2) | 46(1) |
| C(4) | 910(2) | 3798(9) | 1614(2) | 58(1) |
| C(5) | 956(1) | 3162(8) | 2084(2) | 48(1) |
| C(6) | 1160(1) | 1313(8) | 2339(2) | 43(1) |
| C(7) | 1286(1) | 216(8) | 2836(2) | 45(1) |
| C(8) | 1740(2) | −2980(8) | 2365(2) | 49(1) |
| C(9) | 1633(2) | 333(9) | 1288(2) | 54(1) |
| C(10) | 1385(2) | −2495(10) | 869(2) | 64(2) |
| C(11) | 1306(3) | −4438(12) | 534(4) | 113(3) |
| C(12) | 582(2) | 6006(9) | 2048(2) | 67(2) |
| C(13) | 1213(2) | 567(8) | 3248(2) | 56(1) |
| C(14) | 843(2) | 1470(9) | 3088(2) | 55(1) |
| C(15) | 505(2) | 4004(9) | 3261(2) | 58(1) |
| C(16) | 599(2) | 4552(8) | 3812(2) | 56(1) |
| C(17) | 1247(2) | 5284(10) | 4157(2) | 66(2) |
| C(18) | 1160(2) | 4730(9) | 3614(3) | 66(2) |
| C(19) | 923(2) | 7838(10) | 4344(2) | 62(2) |
| C(20) | 575(2) | 8704(9) | 4248(2) | 61(2) |
| C(21) | 269(2) | 9248(10) | 3739(3) | 69(2) |
| C(22) | −38(2) | 10196(11) | 3670(3) | 89(2) |
| C(23) | −38(3) | 10616(17) | 4102(5) | 138(4) |
| C(24) | 271(4) | 10150(20) | 4619(4) | 186(6) |
| C(25) | 580(3) | 9187(16) | 4693(3) | 124(3) |
| C(100) | 2600(1) | 3753(7) | 4292(2) | 45(1) |
| N(101) | 2642(1) | 4084(6) | 3838(2) | 45(1) |
| C(101) | 2226(2) | 4698(9) | 4112(2) | 57(2) |
| O(101) | 1928(1) | 4131(8) | 3578(2) | 66(1) |
| C(102) | 2612(2) | 1344(9) | 4382(2) | 60(2) |
| O(102) | 2286(1) | 338(6) | 3960(2) | 70(1) |
| C(103) | 2924(2) | 4818(10) | 4795(3) | 75(2) |
| O(103) | 3003(3) | 6699(15) | 4729(4) | 79(2) |
| O(1A3) | 3240(4) | 3680(20) | 5004(5) | 69(4) |
| O(1B3) | 2913(8) | 5010(40) | 5196(12) | 93(7) |
| O(1W) | 0 | −1790(80) | 2500 | 151(17) |
| O(201) | 49(9) | 5520(50) | 705(14) | 129(10) |
| C(201) | −372(16) | 4640(90) | −100(20) | 150(20) |
| C(202) | −23(16) | 5270(70) | 270(20) | 111(14) |
| C(203) | 229(17) | 5170(90) | 220(30) | 140(20) |

The present invention is further described in the following examples. All of the examples are actual examples. These examples are not to be construed as limiting the scope of the appended claims.

EXAMPLES

Example 1.1

Form 01-H2-1 of Compound (I)

25 mg of the free acid was dissolved in 1 ml of MeOH. 3 open-ended capillaries were placed in the vial to help stimulate nucleation and crystallization. Slow evaporation at RT afforded square-like plates and crystalline solids of much smaller particle size on the capillaries.

Example 1.2

Form 02-SA-1 of Compound (I)

1. 100 mg of the Compound (I) free acid (0.171 mmol) was mixed with ~0.4 mL of 1N NaOH (0.4 mmol), the final pH was 6.5.
2. IPA (3.5 mL) was added into the clear aq. Solution @ 30-35° C. and slowly cooled to r.t. in ~1 h.

3. Solid was slowly crystallized out from the solution.
4. Allowed the suspension stirred at r.t. for 2 h and the solid was collected by filtration.
5. The filter cake was rinsed with IPS (2×2.5 mL).
6. The resulting solid was dried @ 55° C. under house vacuo to afford 72 mg of white solid.
7. Under microscope, it was semi-crystalline solid.
8. The solid was dissolved with 1.5 mL of EtOH @ 50-55° C. and slow cooled to r.t. in ~1 h.
9. The clear solution was stand at r.t. for 7 days and hair like crystals was observed under microscope.

Example 1.3

Form 03-E.5-1 of Compound (I)

50 mg of mono-TRIS salt was dissolved in 0.2 ml water at RT, then 1.0 ml EtOH was added and a clear solution was obtained. 2 open-ended capillaries were placed in the vial to help stimulate nucleation and crystallization and the vial was covered with Al foil. 2 weeks later thin plate-like crystals were formed on the capillaries.

Example 1.4

Form 03-SA-2 of Compound (I)

50 mg of mono-TRIS salt was first dissolved in 0.2 ml water at RT, then 1.0 ml acetone was added. White precipitation occurred after adding additional 0.6 ml acetone. The vial was heated at 80° C. until a clear solution was obtained. The solution was removed from the heat and cooled naturally to RT. Long thin needles were observed within 2 hours.

Example 1.5

Form 03-DSA-2 of Compound (I)

Preparation of di-tris Salt of Compound (I)-di-tris
1. Combined Compound (I) free acid 0.50 g, in 2 mL H2O, pH 1.02
2. 3M of Tris amine aq. solution was added into the free acid aq. solution to pH to 7.32
3. The crude deep red solution was filtered through a pad of celite, 3 mL H2O was used to rinse the celite pad.
4. Acetone (75 mL) was added slowly into the aq. Solution at room temperature over a period of 1 h, seeded at r.t.
5. After stirring at r.t. for 3 h, the suspension was collected by filtration and rinsed with 150:1 acetone-water (2×5 mL)
6. The solid was dried at high vac. for 3 h and house vac. @ 55° C. for 24 h with nitrogen bleeding.
7. It afforded 0.355 g of product (51% based on SM, 60% based on purity of SM).
8. HPLC showed AP>99%, mother liquor has 5-10% of product.

Preparation of Compound (I)-monotris
9. 0.35 g of di-tris salt in $H_2O$ (3 mL) was added 50 mg (1 eq) TFA to pH was 3.3, reaction was seeded and heated up to 37° C. and slowly heated to 40° C. for 2 h. Acetone. (60 mL) was added into the solution and the solution was slowly cooled to r.t. in ~2 h and white solid was slowly showed up.
10. After stirred at r.t. for 3 h, the white suspension was collected by filtration under N2 and rinsed with acetone (2×10 mL)

The solid was dried under vacuo to afford 0.241 g (80% recovery, 49% from Crude acid) of product, HPLC showed >99% AP and NMR showed 529:tris 1:10~1.01.

Example 2

Single Crystal X-ray Measurements (PXRD)

Single Crystal X-ray Diffraction method was used to characterized some of the samples obtained in Examples 1.1-1.5 using at least the procedure described below. Simulated PXRD is also plotted.

The results are shown in FIGS. 1, 4, 6, 9 and 12.

Table 9 lists the selected PXRD peaks that describe Form 01-H2-1, Form 02-SA-1, Form 03-E.5-1, Form 03-SA-2, and Form 03-DSA-2 of Compound (I).

TABLE 9

Positions (degrees in 2θ) of Selected PXRD Peaks

| Form 01-H2-1 | Form 02-SA-1 | Form 03-E.5-1 | Form 03-SA-2 | Form 03-DSA-2 |
|---|---|---|---|---|
| 5.3 | 4.3 | 5.0 | 5.0 | 5.0 |
| 7.2 | 6.7 | 5.8 | 7.2 | 7.3 |
| 9.7 | 7.4 | 7.2 | 8.2 | 8.3 |
| 10.6 | 8.5 | 8.1 | 9.9 | 10.1 |
| 10.9 | 10.0 | 10.0 | 10.9 | 11.0 |
| 11.7 | 11.8 | 11.0 | 11.8 | 14.4 |
| 13.2 | 12.9 | 11.6 | 14.9 | 15.0 |
| 13.8 | 13.5 | 12.0 | 15.4 | 15.5 |
| 14.5 | 14.1 | 13.2 | 15.9 | 16.0 |
| 15.7 | 14.8 | 16.1 | 16.7 | 17.4 |
| 17.0 | 15.5 | 17.0 | 17.3 | 18.4 |
| 17.7 | 16.0 | 17.5 | 17.7 | 18.9 |
| 18.2 | 16.5 | 19.0 | 20.1 | 19.4 |
| 19.6 | 17.1 | 20.4 | 20.6 | 20.2 |
| 20.3 | 18.5 | 21.1 | 21.9 | 20.6 |

Single Crystal Data (WFD)

A Bruker SMART 2K CCD diffractometer equipped with graphite-monochromated Cu Kα radiation, (λ=1.54056 Å) was used to collect diffraction data at the room temperature. A full data set was collected using the ω scan mode over the 2θ range with a crystal-to-detector distance of 4.98 cm. An empirical absorption correction utilized the SADABS routine associated with the diffractometer (Bruker AXS. 1998, SMART and SAINTPLUS. Area Detector Control and Integration Software, Bruker AXS, Madison, Wis., USA). The final unit cell parameters were determined using the entire data set.

All structures were solved by direct methods and refined by the full-matrix least-squares techniques, using the SHELXTL software package (Sheldrick, G M. 1997, SHELXTL. Structure Determination Programs. Version 5.10, Bruker AXS, Madison, Wis., USA.). The function minimized in the refinements was $\Sigma_w(|F_O|-|F_C|)^2$: R is defined as $\Sigma||F_O|-|F_C||/\Sigma|F_O|$ while $R_w=[\Sigma_w(|F_O|-|F_C|)^2/\Sigma_w|F_O|^2]^{1/2}$, where w is an appropriate weighting function based on errors in the observed intensities. Difference Fourier maps were examined at all stages of refinement. All non-hydrogen atoms were refined with anisotropic thermal displacement parameters. The hydrogen atoms associated with hydrogen bonding were located in the final difference Fourier maps while the positions of the other hydrogen atoms were calculated from an idealized geometry with standard bond lengths and angles. They were assigned isotropic temperature factors and included in structure factor calculations with fixed parameters.

Simulated PXRD Patterns

All the simulated PXRD patterns were calculated from refined atomic coordinates of crystal structures at the room temperature, by using JPOW software (Materials Data Inc. 2001. JPOWD. Powder Diffraction Simulation and Structure Display. Materials Data Inc, Livermore, Calif., USA).

Example 3

Differential Scanning Calorimetry (DSC)

DSC was used to characterized some of the samples obtained in Examples 1.1-1.5 using at least the procedure described below. Simulated PXRD is also plotted.

The results are shown in FIGS. 2, 7, 10 and 13.

DSC (Open Pan)

Differential scanning calorimetry (DSC) experiments were performed in a TA Instruments™ model Q1000 or 2920. The sample (about 2-6 mg) was weighed in an open aluminum pan or sealed pan with pin hole and recorded accurately to a hundredth of a milligram, and transferred to the DSC. The instrument was purged with nitrogen gas at 50 mL/min. Data were collected between room temperature and 300° C. at 10° C./min heating rate. The plot was made with the endothermic peaks pointing down.

Example 4

Thermogravametric Analysis (TGA)

TGA was used to characterized some of the samples obtained in Examples 1.1-1.5 using at least the procedure described below. Simulated PXRD is also plotted.

The results are shown in FIGS. 2, 7, 10 and 13.

TGA (Open Pan)

Thermal gravimetric analysis (TGA) experiments were performed in a TA Instruments™ model Q500 or 2950. The sample (about 10-30 mg) was placed in a platinum pan previously tared. The weight of the sample was measured accurately and recorded to a thousand of a milligram by the instrument The furnace was purged with nitrogen gas at 100 mL/min. Data were collected between room temperature and 300° C. at 10° C./min heating rate.

What is claimed is:

1. A crystalline form of Form 02-SA-1 of Compound (I):

which is a hemiethanolate octahydrate of di-sodium salt with empirical formula of $C_{25}H_{24}N_7O_8P_1Na_2 \cdot 8H_2O \cdot 0.5C_2H_5OH$, characterized by a powder x-ray diffraction pattern comprising four or more 2θ values (CuKα λ=1.5418 Å) selected from the group consisting of 4.3±0.2, 6.7±0.2, 7.4±0.2, 8.5±0.2, 10.0±0.2, 11.8±0.2, 12.9±0.2, 13.5±0.2, 14.1±0.2, 14.8±0.2, 15.5±0.2, 16.0±0.2, 16.5±0.2, 17.1±0.2, 18.5±0.2, at a temperature of about 163K to about 183K.

2. The crystalline form according to claim 1 characterized by unit cell parameters equal to the following:

| Cell dimensions: | a = 6.4392(12)Å |
| --- | --- |
| | α = 99.082(11)° |
| | b = 13.349(2)Å |
| | β = 95.975(12)° |
| | c = 21.041(4)Å |
| | γ = 90.207(12)° |
| Space group: | Triclinic, P-1 |
| Molecules/unit cell | 2 | wherein said crystalline form is at a temperature of about 163K to about 183K.

3. The crystalline form according to claim 1 characterized by: atomic coordinates as listed in Table 4.

4. The crystalline form according to claim 1 further characterized by a powder x-ray diffraction pattern comprising five or more 2θ values (CuKα λ=1.5418 Å) selected from the group consisting of 4.3±0.2, 6.7±0.2, 7.4±0.2, 8.5±0.2, 10.0±0.2, 11.8±0.2, 12.9±0.2, 13.5±0.2, 14.1±0.2, 14.8±0.2, 15.5±0.2, 16.0±0.2, 16.5±0.2, 17.1±0.2, 18.5±0.2, at a temperature of about 163K to about 183K.

5. The crystalline form according to claim 1 characterized by an X-ray powder diffraction (PXRD) pattern, at a temperature of about 20° C. to about 25° C., in accordance with that shown in FIG. 4.

6. A crystalline form of Form 03-E.5-1 of Compound (I):

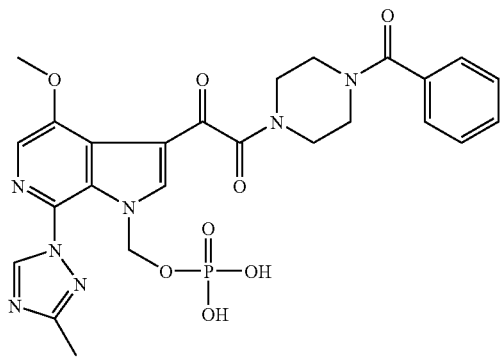

which is a hemiethanolate of mono-TRIS salt with empirical formula of $C_{25}H_{26}N_7O_8P_1 \cdot C_4H_{11}N_1O_3 \cdot 0.5C_2H_5OH$, characterized by a powder x-ray diffraction pattern comprising four or more 2θ values (CuKα λ=1.5418 Å) selected from the group consisting of 5.0±0.2, 5.8±0.2, 7.2±0.2, 8.1±0.2, 10.0±0.2, 11.0±0.2, 11.6±0.2, 12.0±0.2, 13.2±0.2, 16.1±0.2, 17.0±0.2, 17.5±0.2, 19.0±0.2, 20.4±0.2, 21.1±0.2, at a temperature of about 20° C. to about 25° C.

7. The crystalline form according to claim 6 characterized by unit cell parameters equal to the following:

| Cell dimensions: | a = 35.594(2) Å |
| --- | --- |
| | α = 90° |
| | b = 6.2790(4) Å |
| | β = 97.080(3)° |
| | c = 30.6961(19) Å |
| | γ = 90° |
| Space group | Monoclinic, C2/c |
| Molecules/unit cell | 8 | wherein said crystalline form is at a temperature of about 20° C. to about 25° C.

8. The crystalline form according to claim 6 characterized by: atomic coordinates as listed in Table 6.

9. The crystalline form according to claim 6 further characterized by a powder x-ray diffraction pattern comprising five or more 2θ values (CuKα λ=1.5418 Å) selected from the group consisting of 5.0±0.2, 5.8±0.2, 7.2±0.2, 8.1±0.2, 10.0±0.2, 11.0±0.2, 11.6±0.2, 12.0±0.2, 13.2±0.2, 16.1±0.2, 17.0±0.2, 17.5±0.2, 19.0±0.2, 20.4±0.2, 21.1±0.2, at a temperature of about 20° C. to about 25° C.

10. The crystalline form according to claim 6 characterized by an X-ray powder diffraction (PXRD) pattern, at a temperature of about 20° C. to about 25° C., in accordance with that shown in FIG. 6.

11. The crystalline form according to claim 6 characterized by a differential scanning calorimetry (DSC) thermogram in accordance with that shown in FIG. 7.

12. The crystalline form according to claim 6 characterized by a thermo gravimetric analysis (TGA) diagram in accordance with that shown in FIG. 7.

13. A pharmaceutical composition in solid form comprising at least 5 weight % of the crystalline form according to claim 1, based on the weight of the composition, and further comprising a pharmaceutical carrier.

14. The crystalline form according to claim 1, wherein said salt of Compound (I) is substantially pure.

* * * * *